(12) United States Patent
Wilson

(10) Patent No.: US 7,771,372 B2
(45) Date of Patent: Aug. 10, 2010

(54) ULTRASONIC CATHETER WITH AXIAL ENERGY FIELD

(75) Inventor: Richard R. Wilson, Seattle, WA (US)

(73) Assignee: Ekos Corporation, Bothell, WA (US)

( * ) Notice: Subject to any disclaimer, the term of this patent is extended or adjusted under 35 U.S.C. 154(b) by 1312 days.

(21) Appl. No.: 10/751,843

(22) Filed: Jan. 5, 2004

(65) Prior Publication Data

US 2004/0199228 A1    Oct. 7, 2004

Related U.S. Application Data

(60) Provisional application No. 60/438,141, filed on Jan. 3, 2003.

(51) Int. Cl.
*A61N 5/02* (2006.01)

(52) U.S. Cl. .................. 601/2; 600/437; 600/439; 601/1; 606/41; 604/19; 604/20; 604/21; 604/22

(58) Field of Classification Search ................ 600/445, 600/439, 437; 601/2–4
See application file for complete search history.

(56) References Cited

U.S. PATENT DOCUMENTS

| | | |
|---|---|---|
| 3,079,584 A | 2/1963 | Sims |
| 3,433,226 A | 3/1969 | Boyd |
| 4,040,414 A | 8/1977 | Suroff |
| 4,176,662 A | 12/1979 | Frazer |
| 4,319,580 A | 3/1982 | Colley et al. |
| 4,531,943 A | 7/1985 | Van Tassel et al. |
| 4,549,533 A | 10/1985 | Cain et al. |
| 4,739,768 A | 4/1988 | Engelson |
| 4,750,902 A | 6/1988 | Wuchinich et al. |
| 4,808,153 A | 2/1989 | Parisi |
| 4,821,740 A | 4/1989 | Tachibana et al. |
| 4,841,977 A | 6/1989 | Griffith et al. |

(Continued)

FOREIGN PATENT DOCUMENTS

DE    4005743    8/1991

(Continued)

OTHER PUBLICATIONS

Mar. 4, 2009 International Search Report, Application No. PCT/US2004000053.

(Continued)

*Primary Examiner*—Brian Casler
*Assistant Examiner*—John F Ramirez
(74) *Attorney, Agent, or Firm*—Knobbe Martens Olson & Bear, LLP

(57) ABSTRACT

A catheter system for delivering ultrasonic energy to a treatment site within a body lumen comprises a tubular body. The tubular body has a proximal end, a distal end and an energy delivery section positioned between the proximal end and the distal end. The catheter further comprises an inner core configured for insertion into the tubular body. The inner core comprises a first ultrasound radiating member axially separated from a second ultrasound radiating member by an intermediate flexible joint region. The inner core further comprises an electrically conductive portion configured to allow a voltage difference to be applied to at least one of the ultrasound radiating members. The inner core further comprises a high impedance cap positioned proximal to at least one of the ultrasound radiating members.

26 Claims, 22 Drawing Sheets

U.S. PATENT DOCUMENTS

| | | |
|---|---|---|
| 4,870,953 A | 10/1989 | DonMicheal et al. |
| 4,906,238 A | 3/1990 | Greenfeld et al. |
| 4,920,954 A | 5/1990 | Alliger et al. |
| 4,924,863 A | 5/1990 | Sterzer |
| 4,936,281 A | 6/1990 | Stasz |
| 4,948,587 A | 8/1990 | Kost et al. |
| 4,953,565 A | 9/1990 | Tachibana et al. |
| 5,021,044 A | 6/1991 | Sharkawy et al. |
| 5,059,851 A | 10/1991 | Corl et al. |
| 5,069,664 A | 12/1991 | Guess et al. |
| 5,108,369 A | 4/1992 | Ganguly et al. |
| 5,158,071 A | 10/1992 | Umemura et al. |
| 5,163,421 A | 11/1992 | Bernstein et al. |
| 5,197,946 A | 3/1993 | Tachibana |
| 5,226,421 A | 7/1993 | Frisbie et al. |
| 5,250,034 A | 10/1993 | Appling et al. |
| 5,267,954 A | 12/1993 | Nita |
| 5,267,985 A | 12/1993 | Shimada et al. |
| 5,269,291 A | 12/1993 | Carter |
| 5,269,297 A | 12/1993 | Weng et al. |
| 5,271,406 A | 12/1993 | Ganguly et al. |
| 5,282,785 A | 2/1994 | Shapland et al. |
| 5,286,254 A | 2/1994 | Shapland et al. |
| 5,295,484 A | 3/1994 | Marcus et al. |
| 5,304,115 A | 4/1994 | Pflueger et al. |
| 5,307,816 A | 5/1994 | Hashimoto et al. |
| 5,312,328 A | 5/1994 | Nita et al. |
| 5,318,014 A | 6/1994 | Carter |
| 5,327,891 A | 7/1994 | Rammler |
| 5,328,470 A | 7/1994 | Nabel et al. |
| 5,342,292 A | 8/1994 | Mita et al. |
| 5,342,608 A | 8/1994 | Moriya et al. |
| 5,344,395 A | 9/1994 | Whalen et al. |
| 5,344,435 A | 9/1994 | Turner et al. |
| 5,345,940 A | 9/1994 | Seward et al. |
| 5,351,693 A | 10/1994 | Taimisto et al. |
| 5,353,798 A * | 10/1994 | Sieben ................ 600/462 |
| 5,354,279 A | 10/1994 | Hofling |
| 5,362,309 A | 11/1994 | Carter |
| 5,363,853 A | 11/1994 | Lieber et al. |
| 5,368,036 A | 11/1994 | Tanaka et al. |
| 5,368,557 A | 11/1994 | Nita et al. |
| 5,370,675 A | 12/1994 | Edwards et al. |
| 5,380,273 A | 1/1995 | Dubrul et al. |
| 5,382,228 A | 1/1995 | Nita et al. |
| 5,385,148 A | 1/1995 | Lesh et al. |
| 5,397,293 A | 3/1995 | Alliger et al. |
| 5,421,338 A | 6/1995 | Crowley et al. |
| 5,423,797 A | 6/1995 | Adrian et al. |
| 5,427,118 A | 6/1995 | Nita et al. |
| 5,429,136 A | 7/1995 | Milo et al. |
| 5,445,155 A | 8/1995 | Sieben |
| 5,447,509 A | 9/1995 | Mills et al. |
| 5,447,510 A | 9/1995 | Jensen |
| 5,454,795 A | 10/1995 | Samson |
| 5,456,259 A | 10/1995 | Barlow et al. |
| 5,458,568 A | 10/1995 | Racchini et al. |
| 5,462,523 A | 10/1995 | Samson et al. |
| 5,465,726 A | 11/1995 | Dickinson et al. |
| 5,474,531 A | 12/1995 | Carter |
| 5,496,267 A | 3/1996 | Drasler et al. |
| 5,496,294 A | 3/1996 | Hergenrother et al. |
| 5,498,238 A | 3/1996 | Shapland et al. |
| 5,503,155 A | 4/1996 | Salmon et al. |
| 5,509,896 A | 4/1996 | Carter |
| 5,514,092 A | 5/1996 | Forman et al. |
| 5,520,189 A | 5/1996 | Malinowski et al. |
| 5,523,058 A | 6/1996 | Umemura et al. |
| 5,531,715 A | 7/1996 | Engelson et al. |
| 5,533,986 A | 7/1996 | Mottola et al. |
| 5,542,917 A | 8/1996 | Nita et al. |
| 5,558,092 A | 9/1996 | Unger et al. |
| 5,560,362 A | 10/1996 | Sliwa, Jr. et al. |
| 5,569,197 A | 10/1996 | Helmus et al. |
| 5,571,086 A | 11/1996 | Kaplan et al. |
| 5,588,432 A | 12/1996 | Crowley |
| 5,599,326 A | 2/1997 | Carter |
| 5,603,694 A | 2/1997 | Brown et al. |
| 5,606,974 A | 3/1997 | Castellano et al. |
| 5,609,574 A | 3/1997 | Kaplan et al. |
| 5,618,275 A | 4/1997 | Bock |
| 5,620,479 A | 4/1997 | Diederich |
| 5,628,728 A | 5/1997 | Tachibana et al. |
| 5,628,730 A | 5/1997 | Shapland et al. |
| 5,630,837 A | 5/1997 | Crowley |
| 5,656,016 A | 8/1997 | Ogden |
| 5,695,460 A | 12/1997 | Siegel et al. |
| 5,713,831 A | 2/1998 | Olsson |
| 5,713,848 A | 2/1998 | Dubrul et al. |
| 5,725,494 A | 3/1998 | Brisken |
| 5,728,062 A | 3/1998 | Brisken |
| 5,733,315 A | 3/1998 | Burdette et al. |
| 5,735,811 A | 4/1998 | Brisken |
| 5,759,173 A | 6/1998 | Preissman et al. |
| 5,779,673 A | 7/1998 | Roth et al. |
| 5,807,395 A * | 9/1998 | Mulier et al. ................. 606/41 |
| 5,827,313 A | 10/1998 | Ream |
| 5,827,529 A | 10/1998 | Ono et al. |
| 5,836,896 A | 11/1998 | Rosenschein |
| 5,836,946 A | 11/1998 | Diaz et al. |
| 5,840,031 A | 11/1998 | Crowley |
| 5,842,994 A | 12/1998 | TenHoff et al. |
| 5,846,218 A | 12/1998 | Brisken et al. |
| 5,876,345 A | 3/1999 | Eaton et al. |
| 5,895,398 A | 4/1999 | Wensel et al. |
| 5,916,192 A | 6/1999 | Nita et al. |
| 5,928,186 A | 7/1999 | Homsma et al. |
| 5,931,805 A | 8/1999 | Brisken |
| 5,941,868 A | 8/1999 | Kaplan et al. |
| 5,951,494 A | 9/1999 | Wang et al. |
| 5,971,949 A | 10/1999 | Levin et al. |
| 5,976,120 A | 11/1999 | Chow et al. |
| 5,989,274 A | 11/1999 | Dacison et al. |
| 5,997,497 A | 12/1999 | Nita et al. |
| 6,001,069 A | 12/1999 | Tachibana et al. |
| 6,004,269 A | 12/1999 | Crowley et al. |
| 6,024,703 A | 2/2000 | Zanelli et al. |
| 6,024,718 A | 2/2000 | Chen et al. |
| 6,053,868 A | 4/2000 | Geistert et al. |
| 6,059,731 A | 5/2000 | Seward et al. |
| 6,063,069 A | 5/2000 | Cragg et al. |
| 6,078,830 A | 6/2000 | Levin et al. |
| 6,096,000 A | 8/2000 | Tachibana et al. |
| 6,110,314 A | 8/2000 | Nix et al. |
| 6,113,558 A | 9/2000 | Rosenschein et al. |
| 6,120,454 A | 9/2000 | Suorsa et al. |
| 6,135,971 A | 10/2000 | Hutchinsons et al. |
| 6,135,976 A | 10/2000 | Tachibana et al. |
| 6,149,599 A | 11/2000 | Schlesinger |
| 6,176,842 B1 | 1/2001 | Tachibana et al. |
| 6,182,666 B1 | 2/2001 | Dobak, III |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,241,692 B1 | 6/2001 | Tu et al. |
| 6,241,703 B1 | 6/2001 | Levin et al. |
| 6,261,246 B1 | 7/2001 | Pantages et al. |
| 6,277,077 B1 | 8/2001 | Brisken et al. |
| 6,287,271 B1 | 9/2001 | Dubrul et al. |

| | | |
|---|---|---|
| 6,296,619 B1 | 10/2001 | Brisken et al. |
| 6,361,500 B1 | 3/2002 | Masters |
| 6,361,531 B1 | 3/2002 | Hissong |
| 6,368,315 B1 | 4/2002 | Gillis et al. |
| 6,372,498 B2 | 4/2002 | Newman et al. |
| 6,379,320 B1 * | 4/2002 | Lafon et al. .................. 601/3 |
| 6,387,035 B1 | 5/2002 | Jung, Jr. et al. |
| 6,423,026 B1 | 7/2002 | Gesswein et al. |
| 6,433,464 B2 | 8/2002 | Jones |
| 6,437,487 B1 | 8/2002 | Mohr, III et al. |
| 6,461,314 B1 | 10/2002 | Pant et al. |
| 6,464,680 B1 | 10/2002 | Brisken et al. |
| 6,508,775 B2 | 1/2003 | McKenzie et al. |
| 6,524,251 B2 | 2/2003 | Rabiner et al. |
| 6,524,300 B2 | 2/2003 | Meglin |
| 6,537,224 B2 | 3/2003 | Mauchamp et al. |
| 6,551,337 B1 | 4/2003 | Rabiner et al. |
| 6,554,801 B1 | 4/2003 | Steward et al. |
| 6,561,998 B1 | 5/2003 | Roth et al. |
| 6,562,021 B1 | 5/2003 | Derbin et al. |
| 6,579,279 B1 | 6/2003 | Rabiner et al. |
| 6,582,392 B1 | 6/2003 | Bennett et al. |
| 6,585,763 B1 | 7/2003 | Keilman et al. |
| 6,589,182 B1 | 7/2003 | Loftman et al. |
| 6,599,288 B2 | 7/2003 | Maguire et al. |
| 6,605,084 B2 | 8/2003 | Acker et al. |
| 6,607,502 B1 | 8/2003 | Maguire et al. |
| 6,635,017 B1 | 10/2003 | Moehring et al. |
| 6,647,755 B2 | 11/2003 | Rabiner et al. |
| 6,652,547 B2 | 11/2003 | Rabiner et al. |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,692,494 B1 | 2/2004 | Cooper et al. |
| 6,711,953 B2 * | 3/2004 | Hayashi et al. ................ 73/626 |
| 6,723,063 B1 | 4/2004 | Zhang et al. |
| 6,740,040 B1 * | 5/2004 | Mandrusov et al. ......... 600/439 |
| 6,758,857 B2 | 7/2004 | Cioanta et al. |
| 6,824,515 B2 * | 11/2004 | Suorsa et al. ................ 600/439 |
| 6,855,123 B2 | 2/2005 | Nita |
| 6,958,040 B2 | 10/2005 | Oliver et al. |
| 6,979,293 B2 * | 12/2005 | Hansmann et al. .......... 600/439 |
| 7,001,336 B2 * | 2/2006 | Mandrusov et al. ......... 600/439 |
| 7,089,063 B2 | 8/2006 | Lesh et al. |
| 2001/0037106 A1 | 11/2001 | Shadduck |
| 2002/0000763 A1 | 1/2002 | Jones |
| 2002/0032394 A1 | 3/2002 | Brisken et al. |
| 2002/0099292 A1 | 7/2002 | Brisken et al. |
| 2002/0133111 A1 | 9/2002 | Shadduck |
| 2002/0151825 A1 | 10/2002 | Rubenchik et al. |
| 2003/0004439 A1 * | 1/2003 | Pant et al. ........................ 601/2 |
| 2003/0023261 A1 | 1/2003 | Tomaschko et al. |
| 2003/0028173 A1 | 2/2003 | Forsberg |
| 2003/0036705 A1 | 2/2003 | Hare et al. |
| 2003/0040501 A1 | 2/2003 | Newman et al. |
| 2003/0040698 A1 | 2/2003 | Makin et al. |
| 2003/0069525 A1 | 4/2003 | Brisken |
| 2003/0109812 A1 | 6/2003 | Corl et al. |
| 2003/0220568 A1 | 11/2003 | Hansmann et al. |
| 2003/0236539 A1 | 12/2003 | Rabiner |
| 2004/0015084 A1 | 1/2004 | Flesch et al. |
| 2004/0015122 A1 | 1/2004 | Zhang et al. |
| 2004/0015138 A1 | 1/2004 | Currier et al. |
| 2004/0019318 A1 | 1/2004 | Wilson et al. |
| 2004/0024347 A1 | 2/2004 | Wilson et al. |
| 2004/0024393 A1 | 2/2004 | Nita et al. |
| 2004/0039311 A1 | 2/2004 | Nita et al. |
| 2004/0049148 A1 | 3/2004 | Rodriguez et al. |
| 2004/0068189 A1 | 4/2004 | Wilson et al. |
| 2005/0043753 A1 | 2/2005 | Rabiner et al. |
| 2005/0288695 A1 | 12/2005 | Jenson et al. |

FOREIGN PATENT DOCUMENTS

| | | |
|---|---|---|
| EP | 0 629 382 | 12/1994 |
| EP | 0774232 | 5/1997 |
| EP | 1 090 658 | 4/2001 |
| EP | 1 103 281 | 5/2001 |
| GB | 155 004 A | 8/1979 |
| JP | 2-180275 | 7/1990 |
| WO | WO 89/04142 | 5/1989 |
| WO | WO 92/00113 | 1/1992 |
| WO | WO 95/01751 | 1/1995 |
| WO | WO 95/26777 | 10/1995 |
| WO | WO 96/29935 | 10/1996 |
| WO | WO 97/19644 | 6/1997 |
| WO | WO 97/19645 A1 | 6/1997 |
| WO | WO 98/18391 | 5/1998 |
| WO | WO 98/48711 | 11/1998 |
| WO | WO 99/33500 | 7/1999 |
| WO | WO 99/34858 | 7/1999 |
| WO | WO 99/44512 | 9/1999 |
| WO | WO 00/00095 | 1/2000 |
| WO | WO 00/38580 | 7/2000 |
| WO | WO 01/13357 | 2/2001 |
| WO | WO 01/54754 | 8/2001 |
| WO | WO 01/95788 | 12/2001 |
| WO | WO 02/13678 | 2/2002 |
| WO | WO 03/051208 | 6/2003 |
| WO | WO 03/065908 | 8/2003 |

OTHER PUBLICATIONS

Hynynen et al.; "Small Cylindrical Ultrasound Sources for Induction of Hyperthermia via Body Cavities or Interstitial implants", Arizona Cancer, 1993.

Lee et al.; "arrays of Multielement Ultrasound Applications for Interstital Hyperthermia"; IEEE Transactions on Biomedical Engineering; vol. 46, No., Jul. 1999.

* cited by examiner

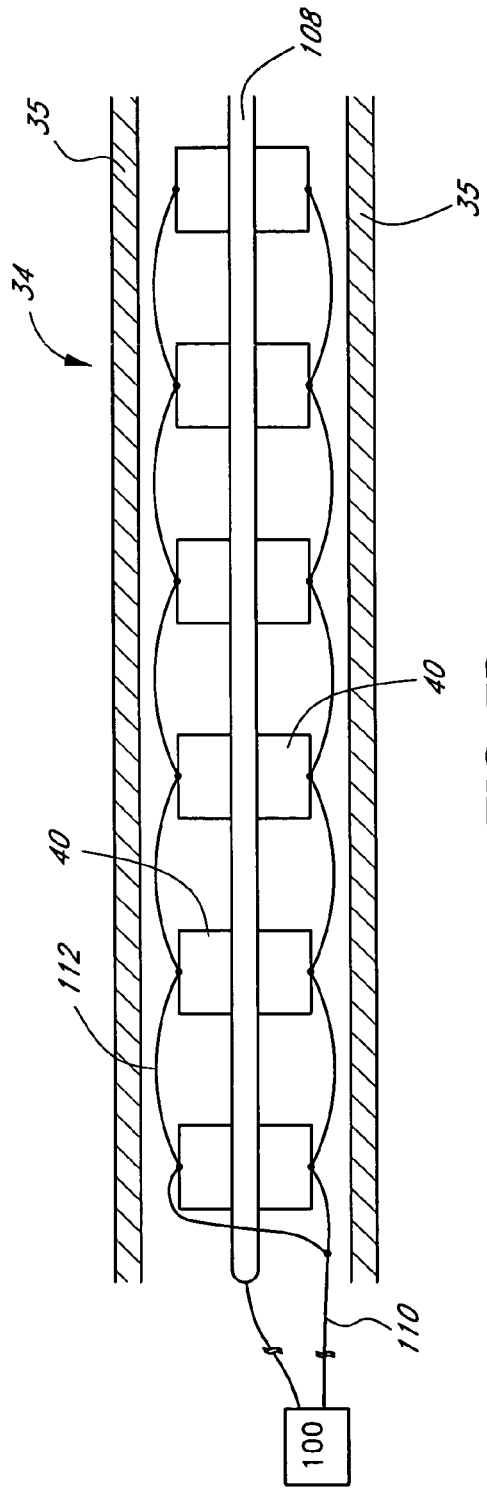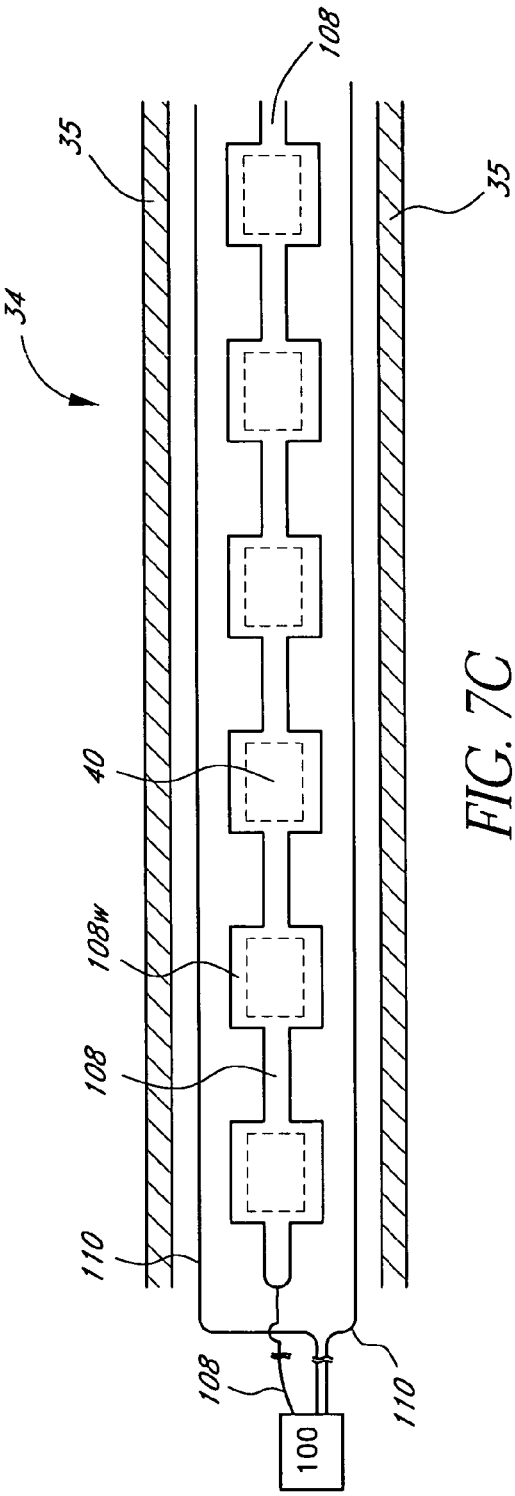

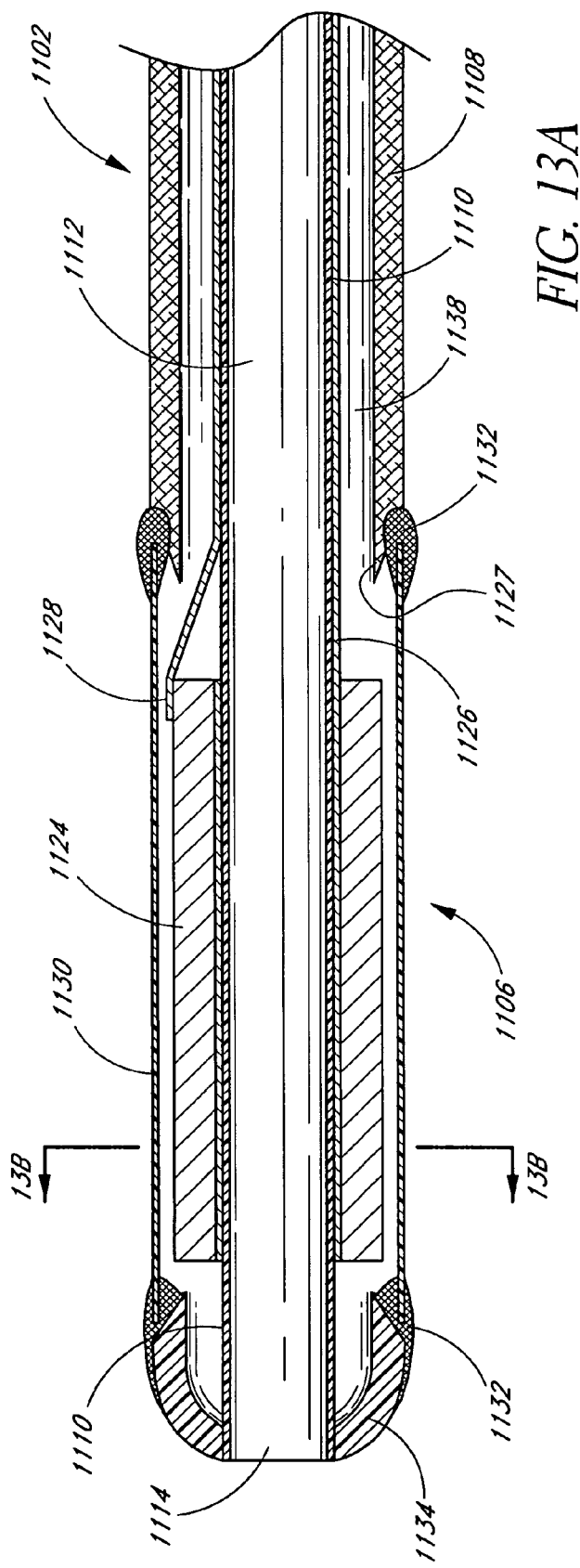
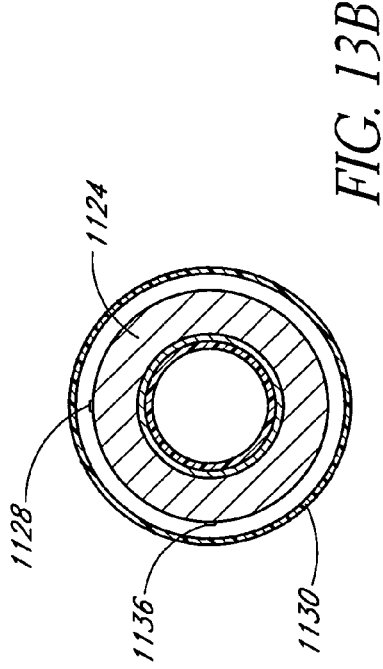
FIG. 13A
FIG. 13B

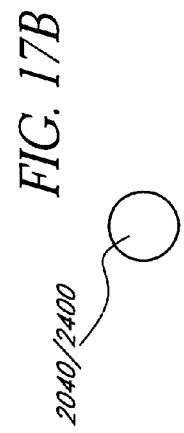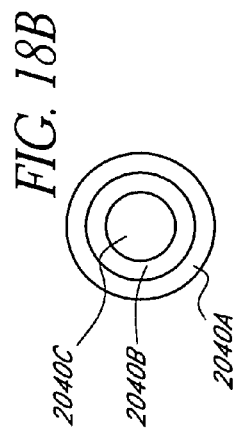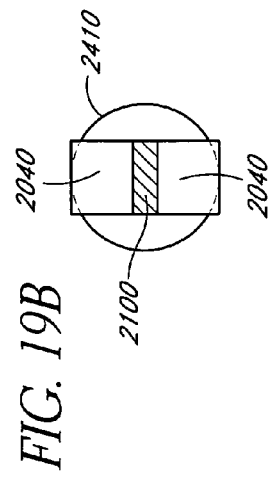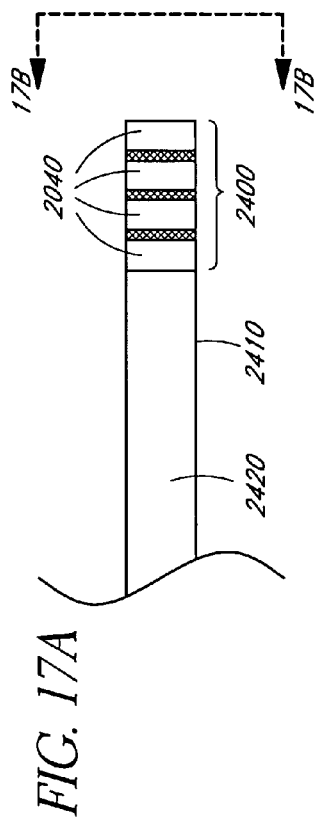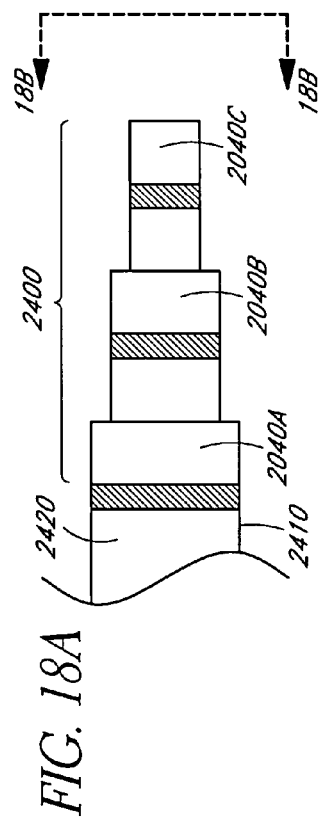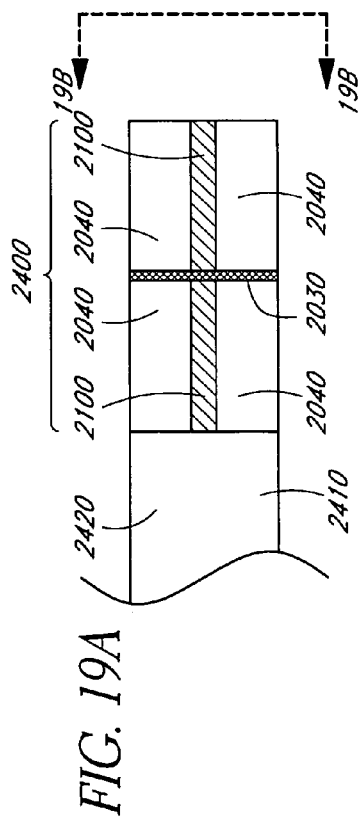

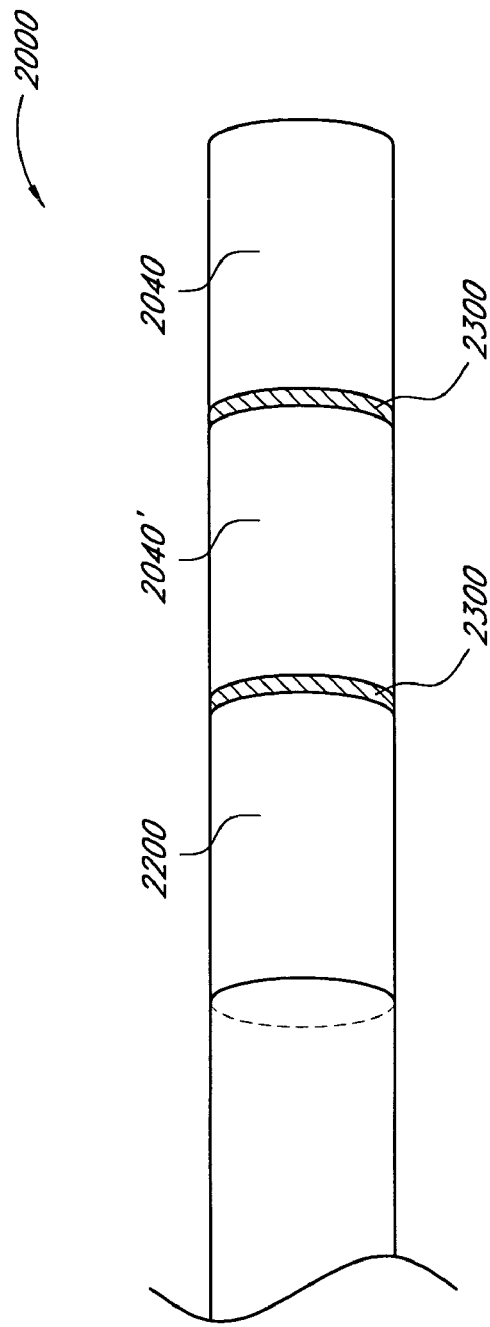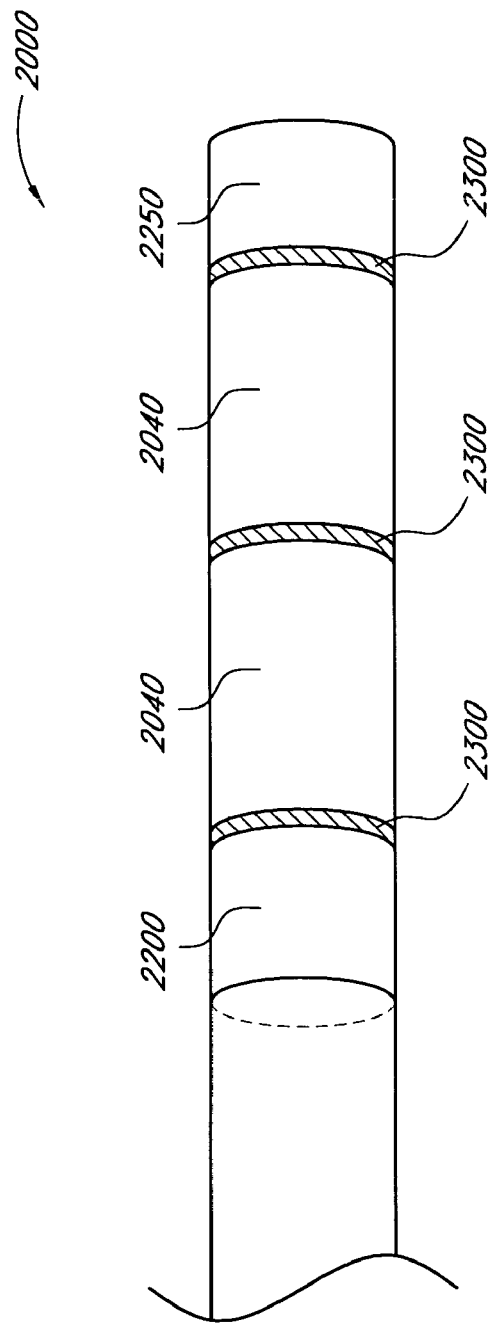

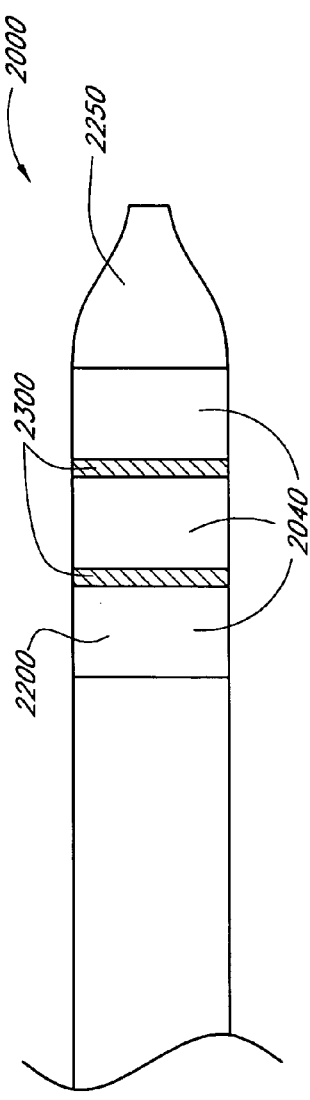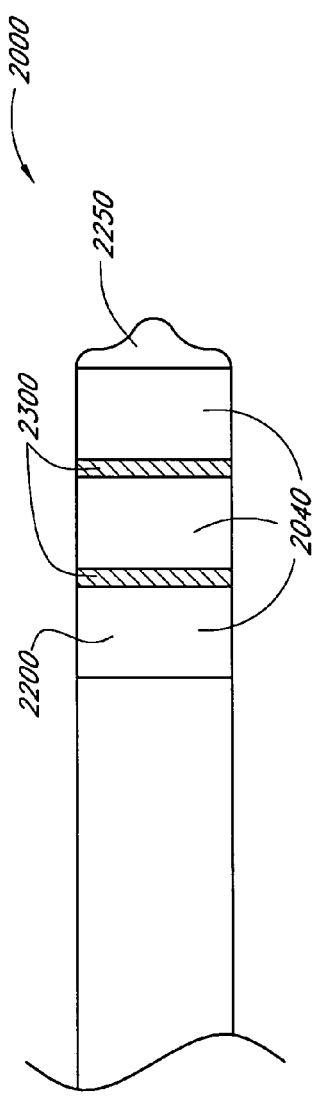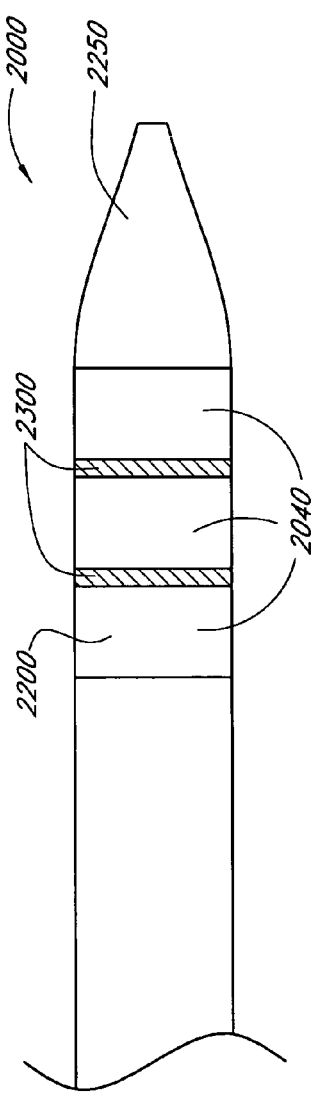

ULTRASONIC CATHETER WITH AXIAL ENERGY FIELD

PRIORITY APPLICATION

This application claims the benefit of U.S. Provisional Application 60/438,141, filed 3 Jan. 2003. This priority application is hereby incorporated by reference herein in its entirety.

FIELD OF THE INVENTION

The present invention relates generally to ultrasonic catheters, and more specifically to ultrasonic catheters configured to deliver ultrasonic energy and a therapeutic compound to a treatment site.

BACKGROUND OF THE INVENTION

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site within a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing therapeutic compounds directly to the occlusion site. Ultrasonic energy generated by the ultrasound assembly enhances the effect of the therapeutic compounds. Such a device can be used in the treatment of diseases such as peripheral arterial occlusion or deep vein thrombosis. In such applications, the ultrasonic energy enhances treatment of the occlusion with therapeutic compounds such as urokinase, tissue plasminogen activator ("tPA"), recombinant tissue plasminogen activator ("rtPA") and the like. Further information on enhancing the effect of a therapeutic compound using ultrasonic energy is provided in U.S. Pat. Nos. 5,318,014, 5,362,309, 5,474,531, 5,628,728, 6,001,069 and 6,210,356.

Ultrasonic catheters can also be used to enhance gene therapy at a treatment site within the patient's body. For example, U.S. Pat. No. 6,135,976 discloses an ultrasonic catheter having one or more expandable sections capable of occluding a section of a body lumen, such as a blood vessel. A gene therapy composition is then delivered to the occluded portion of the vessel through the catheter fluid delivery lumen. Ultrasonic energy generated by the ultrasound assembly is applied to the occluded vessel, thereby enhancing the delivery of a genetic composition into the cells of the occluded vessel.

Ultrasonic catheters can also be used to enhance delivery and activation of light activated drugs. For example, U.S. Pat. No. 6,176,842 discloses methods for using an ultrasonic catheter to treat biological tissues by delivering a light activated drug to the biological tissues and exposing the light activated drug to ultrasonic energy.

SUMMARY OF THE INVENTION

In certain applications, it is desirable to project an axial ultrasonic energy field from the distal end of an ultrasonic catheter. Such a field, also referred to as a "forward-facing" field, is useful in many of the aforementioned applications, including clot dissolution and gene therapy. In particular, a high-power, forward-facing ultrasonic energy field is useful in the dissolution of an aged blood clot located in the coronary vasculature. Thus, a ultrasonic catheter that is capable of producing such an energy field, and that is also compatible with conventional cardiological practice, has been developed.

In accordance with the foregoing, in an exemplary embodiment, a catheter system for delivering ultrasonic energy to a treatment site within a body lumen comprises a tubular body. The tubular body has a proximal end, a distal end and an energy delivery section positioned between the proximal end and the distal end. The catheter further comprises an inner core configured for insertion into the tubular body. The inner core comprises a first ultrasound radiating member axially separated from a second ultrasound radiating member by an intermediate flexible joint region. The inner core further comprises an electrically conductive portion configured to allow a voltage difference to be applied to at least one of the ultrasound radiating members. The inner core further comprises a high impedance cap positioned proximal to at least one of the ultrasound radiating members.

In another exemplary embodiment, an ultrasound assembly comprises an elongate member having a proximal region and a distal region opposite the proximal region. A high impedance cap is positioned adjacent to the elongate member distal region. The ultrasound assembly further comprises an ultrasound radiating member positioned distal to the high impedance cap. The ultrasound radiating member is configured to generate a distribution of ultrasonic energy that has a greater density in a region axially distal to the ultrasound radiating member than in an annular region surrounding the ultrasound radiating member.

In another exemplary embodiment, an apparatus comprises a tubular body having a proximal end, a distal end opposite the proximal end, and a treatment zone located between the distal end and the proximal end. The apparatus further comprises a plurality of fluid delivery lumens defined within the tubular body. The apparatus further comprises an inner core comprising a high impedance cap and at least one ultrasound radiating member positioned distal to the high impedance cap. The apparatus further comprises a plurality of cooling fluid channels defined between at least an inner surface of the tubular body and an outer surface of the inner core. Each cooling fluid channel is positioned generally radially between two fluid delivery lumens.

BRIEF DESCRIPTION OF THE DRAWINGS

Exemplary embodiments of the ultrasonic catheter disclosed herein are illustrated in the accompanying drawings, which are for illustrative purposes only. The drawings comprise the following figures, in which like numerals indicate like parts.

FIG. 7B is a cross-sectional view of the ultrasound assembly of FIG. 7A taken along line 7B-7B.

FIG. 7C is a cross-sectional view of the ultrasound assembly of FIG. 7A taken along line 7C-7C.

FIG. 13A is a cross-sectional view of a distal end of the ultrasound catheter of FIG. 12.

FIG. 13B is a cross-sectional view of the ultrasound catheter of FIG. 12 taken through line 13B-13B of FIG. 13A.

FIG. 17A is a cross-sectional view of a distal end of a catheter guidewire configured to produce a forward-facing ultrasonic energy field and comprising a plurality of ultrasound radiating members with substantially similar dimensions.

FIG. 17B is a cross-sectional view of the catheter guidewire of FIG. 17A taken along line 17B-17B.

FIG. 18A is a cross-sectional view of a distal end of a catheter guidewire configured to produce a forward-facing ultrasonic energy field and comprising a plurality of ultrasound radiating members with varying dimensions.

FIG. 18B is a cross-sectional view of the catheter guidewire of FIG. 18A taken along line 18B-18B.

FIG. 19A is a cross-sectional view of a distal end of a catheter guidewire configured to produce a forward-facing ultrasonic energy field and comprising a plurality of ultrasound radiating members with rectangular dimensions.

FIG. 19B is a cross-sectional view of the catheter guidewire of FIG. 19A taken along line 19B-19B.

FIG. 20 is a side view of a distal end of an ultrasonic catheter configured to produce a forward-facing ultrasonic energy field and comprising a proximal end joint.

FIG. 21 is a side view of a distal end of an ultrasonic catheter configured to produce a forward-facing ultrasonic energy field and comprising a flat distal horn.

FIG. 22 is a cross-sectional view of a distal end of an ultrasonic catheter configured to produce a forward-facing ultrasonic energy field and comprising a blunt distal horn.

FIG. 23 is a cross-sectional view of a distal end of an ultrasonic catheter configured to produce a forward-facing ultrasonic energy field and comprising a short pointed distal horn.

FIG. 24 is a cross-sectional view of a distal end of an ultrasonic catheter configured to produce a forward-facing ultrasonic energy field and comprising a long pointed distal horn.

DETAILED DESCRIPTION OF PREFERRED EMBODIMENTS

Figure 1:
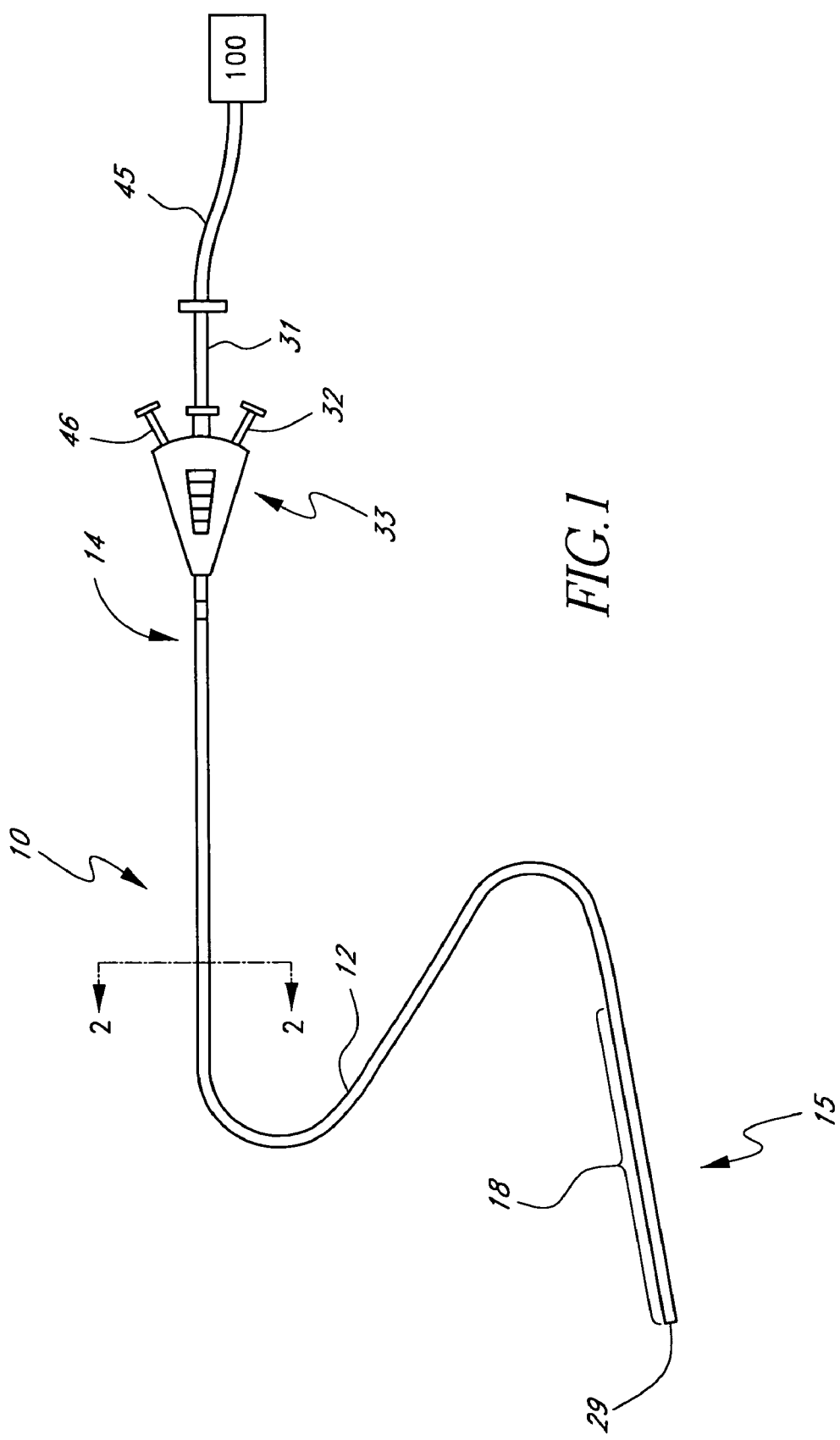
FIG. 1 is a schematic illustration of an ultrasonic catheter configured for insertion into large vessels of the human body.

As described above, ultrasonic catheters capable of delivering multi-frequency ultrasonic energy and/or forward-facing ultrasonic energy fields to a treatment site within a patient's vasculature have been developed. Exemplary embodiments of these ultrasonic catheters, including exemplary methods of use, are described herein.

The ultrasonic catheters described herein can be used to enhance the therapeutic effects of therapeutic compounds at a treatment site within a patient's body. As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069, 6,096,000, 6,210,356 and 6,296,619. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing heparin, urokinase, streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,269,291 and 5,431,663. Further information about using cavitation to produce biological effects can be found in U.S. Pat. RE36,939.

The ultrasonic catheters described herein are configured for applying ultrasonic energy over a substantial length of a body lumen, such as, for example, the larger vessels located in the leg. However, it should be appreciated that certain features and aspects of the present invention may be applied to catheters configured to be inserted into the small cerebral vessels, in solid tissues, in duct systems and in body cavities. Such catheters are described in U.S. patent application Ser. No. 10/309,417, entitled "Small Vessel Ultrasound Catheter" and filed Dec. 3, 2002, the entire disclosure of which is hereby incorporated herein by reference. Additional embodiments that may be combined with certain features and aspects of the embodiments described herein are described in U.S. patent application Ser. No. 10/291,891, entitled "Ultrasound Assembly For Use With A Catheter" and filed Nov. 7, 2002, the entire disclosure of which is hereby incorporated herein by reference.

For purposes of summarizing the invention and the advantages achieved over the prior art, certain objects and advantages of the invention have been described above. It is to be understood that not necessarily all such objects or advantages may be achieved in accordance with any particular embodiment of the invention. Thus, for example, the invention may be embodied or carried out in a manner that achieves or optimizes one advantage or group of advantages as taught herein without necessarily achieving other objects or advantages as may be taught or suggested herein.

The embodiments disclosed herein are intended to be within the scope of the present invention. These and other embodiments should be apparent based on the following detailed description, which refers to the attached figures. The present invention is not limited to any particular disclosed embodiment, but is limited only by the claims set forth herein.

Overview of a Large Vessel Ultrasound Catheter.

With initial reference to FIG. 1, an ultrasonic catheter 10 configured for use in the large vessels of a patient's anatomy is schematically illustrated. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally comprises a multi-component, elongate flexible tubular body 12 having a proximal region 14 and a distal region 15. The tubular body 12 includes a flexible energy delivery section 18 and a distal exit port 29 located in the distal region 15 of the catheter 10. A backend hub 33 is attached to the proximal region 14 of the tubular body 12, the backend hub 33 comprising a proximal access port 31, an inlet port 32 and a cooling fluid fitting 46. The proximal access port 31 can be connected to control circuitry 100 via cable 45.

The tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 may be formed from the same material or a material of the same thickness as the proximal region 14.

In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter 10. The third section, which preferably includes the energy delivery section 18, generally has a lower stiffness than the second section.

Figure 2:
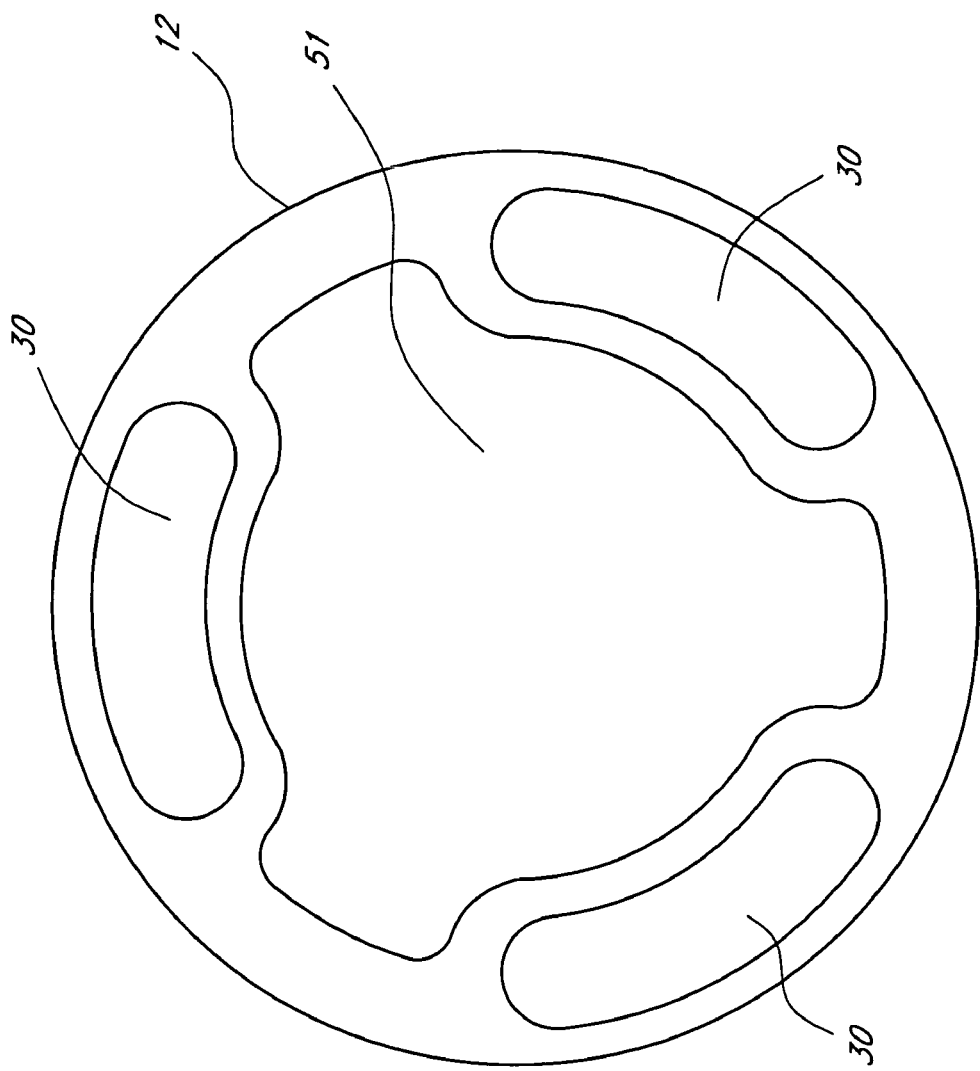
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub 33 preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
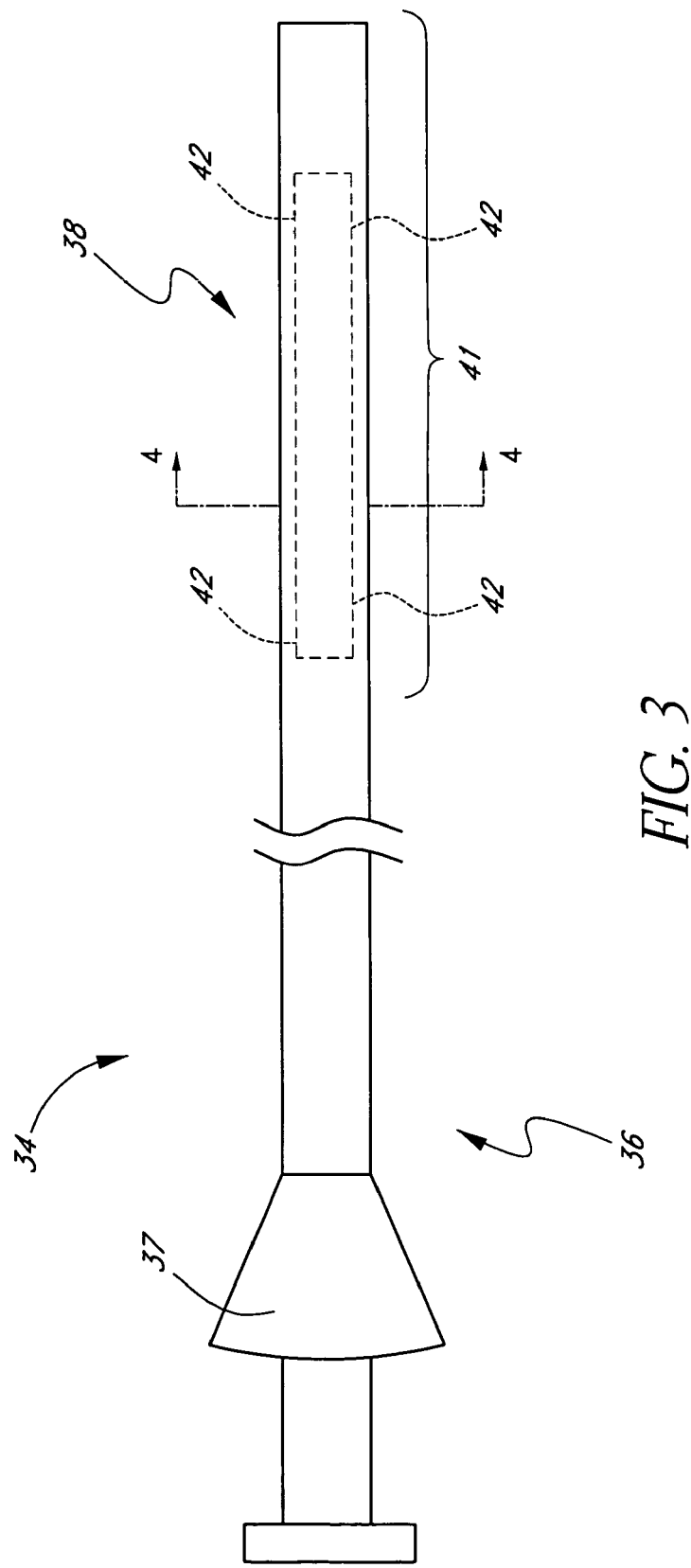
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members form an ultrasound assembly 42, which will be described in greater detail below.

Figure 4:
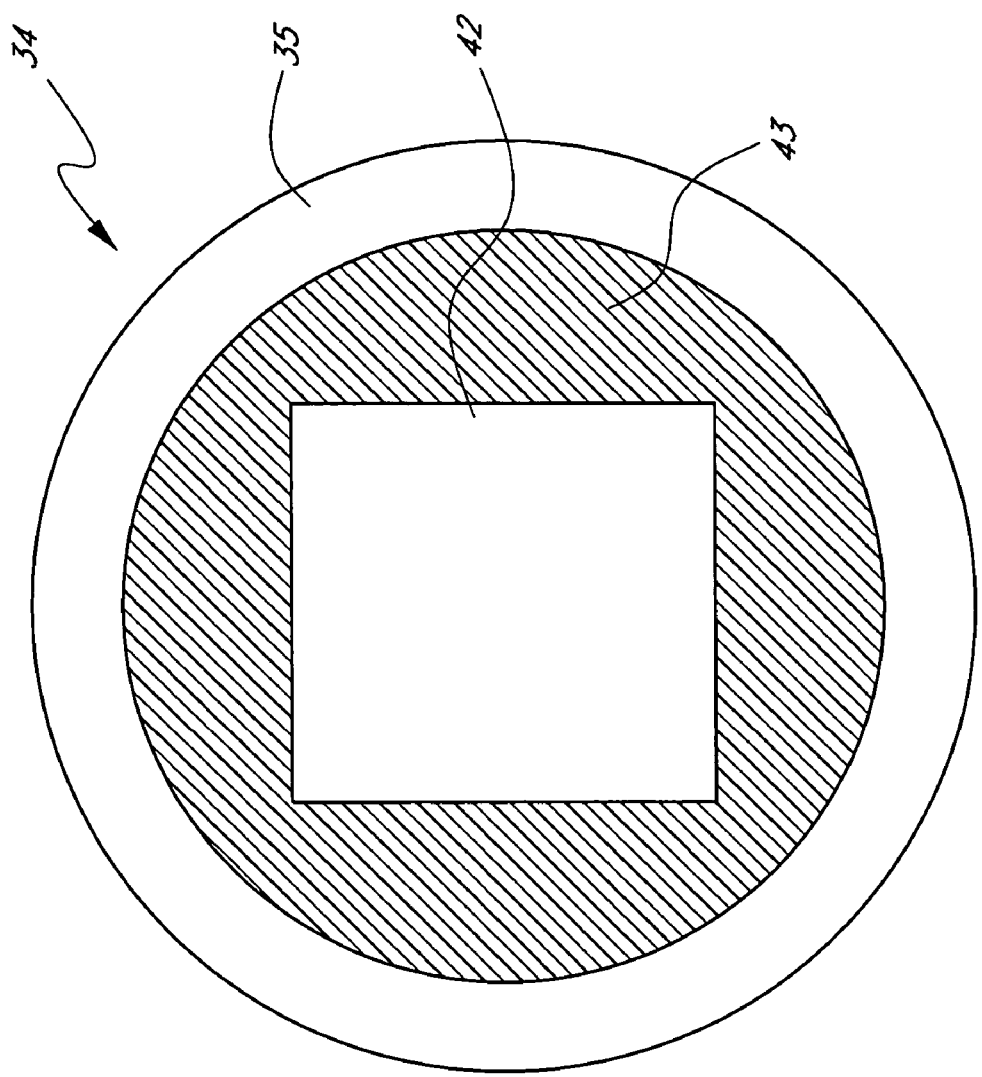
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, in an exemplary embodiment, the inner core 34 includes a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to control circuitry 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
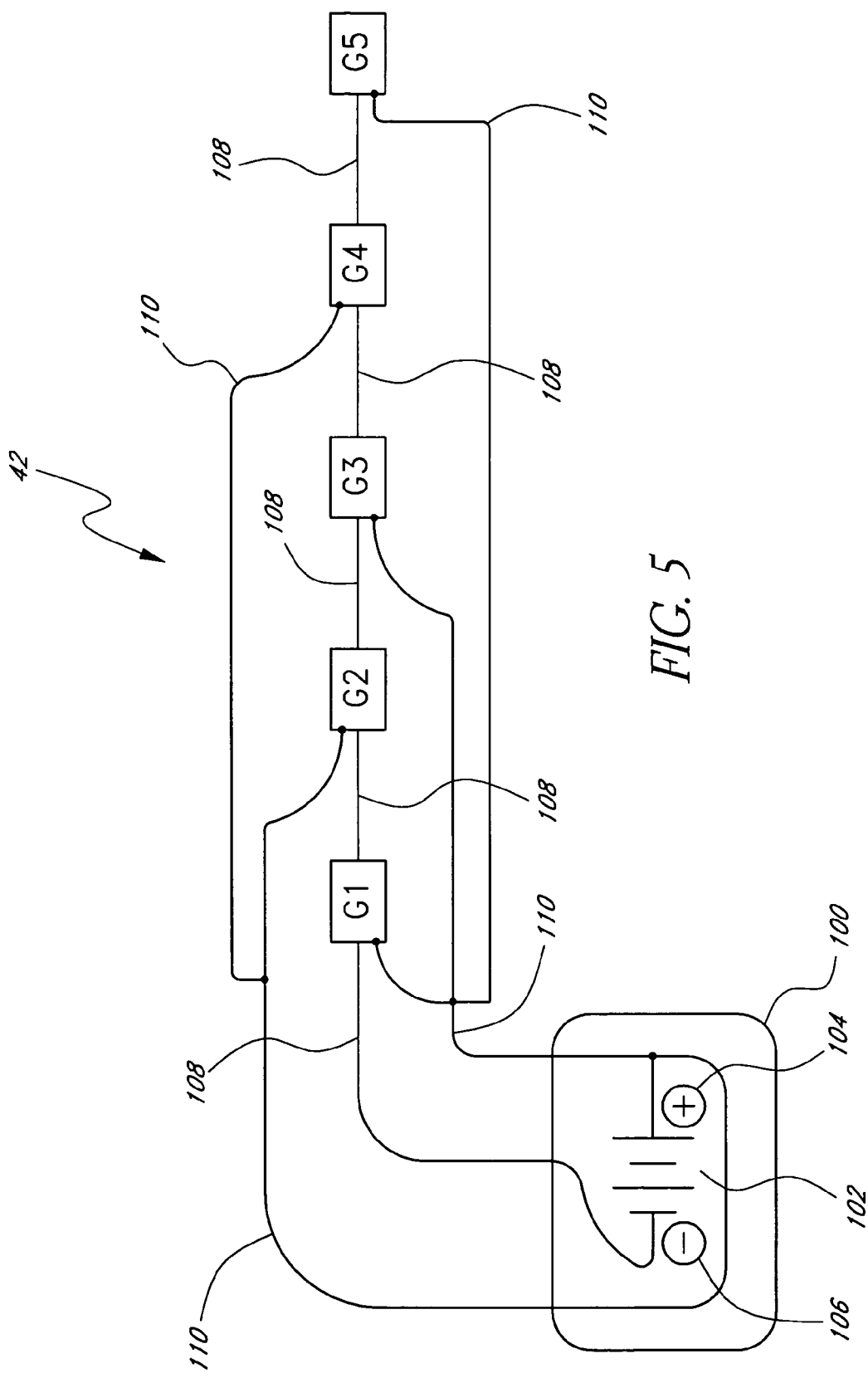
FIG. 5 is a schematic wiring diagram illustrating an exemplary technique for electrically connecting five groups of ultrasound radiating members to form an ultrasound assembly.
Figure 6:
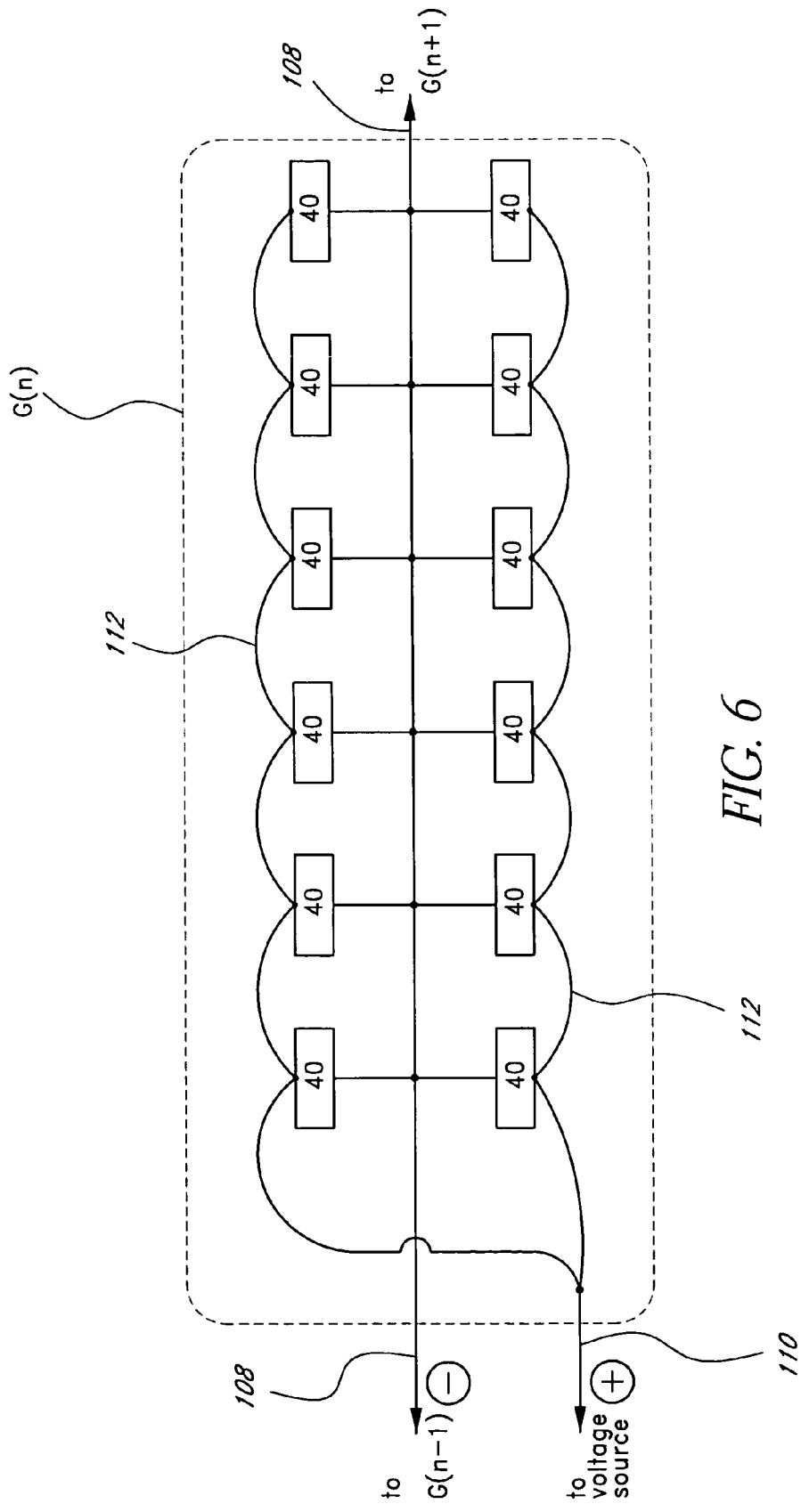
FIG. 6 is a schematic wiring diagram illustrating an exemplary technique for electrically connecting one of the groups of FIG. 5.

In an exemplary embodiment, the ultrasound assembly 42 comprises a plurality of ultrasound radiating members 40 that are divided into one or more groups G1, G2, G3, . . . G(n). For example, FIGS. 5 and 6 are schematic wiring diagrams illustrating one technique for connecting five groups of ultrasound radiating members to form the ultrasound assembly 42. As illustrated in FIG. 5, the ultrasound assembly 42 comprises five groups G1, G2, G3, G4, G5 of ultrasound radiating members that are electrically connected to each other. The five groups are also electrically connected to the control circuitry 100. FIG. 6 is a schematic wiring diagram illustrating an example group G(n) which compromises a plurality of ultrasound radiating members 40.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
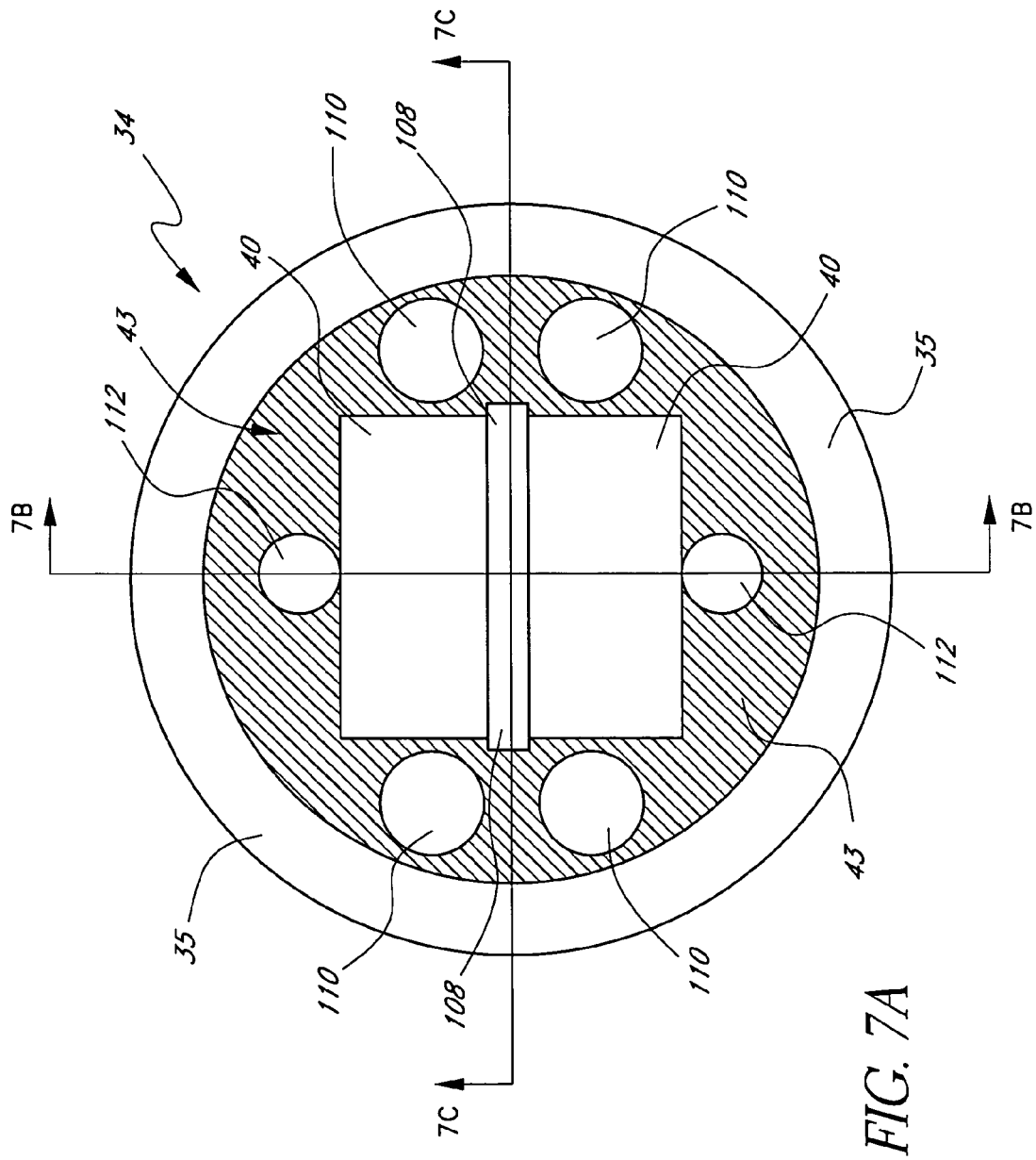
FIG. 7A is a schematic illustration of the ultrasound assembly of FIG. 5 housed within the inner core of FIG. 4.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
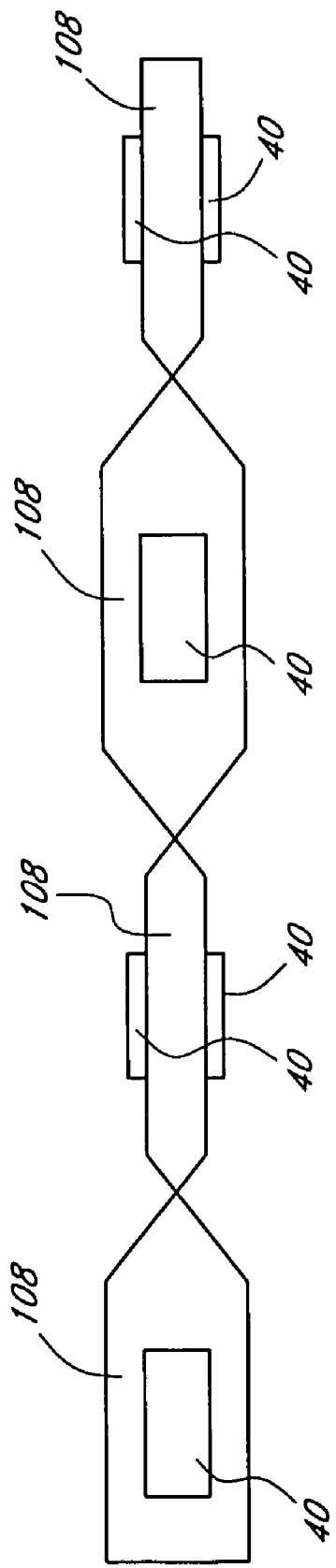
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

The wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focussed, more diffuse ultrasonic energy field to the treatment site.

In an exemplary embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36-gauge electrical conductors, while positive contact wires 112 are preferably 42-gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment the frequency is between about 1 MHz and 3 MHz. In yet another embodiment, the ultrasound radiating members 40 are operated with a frequency of about 2 MHz.

Figure 8:
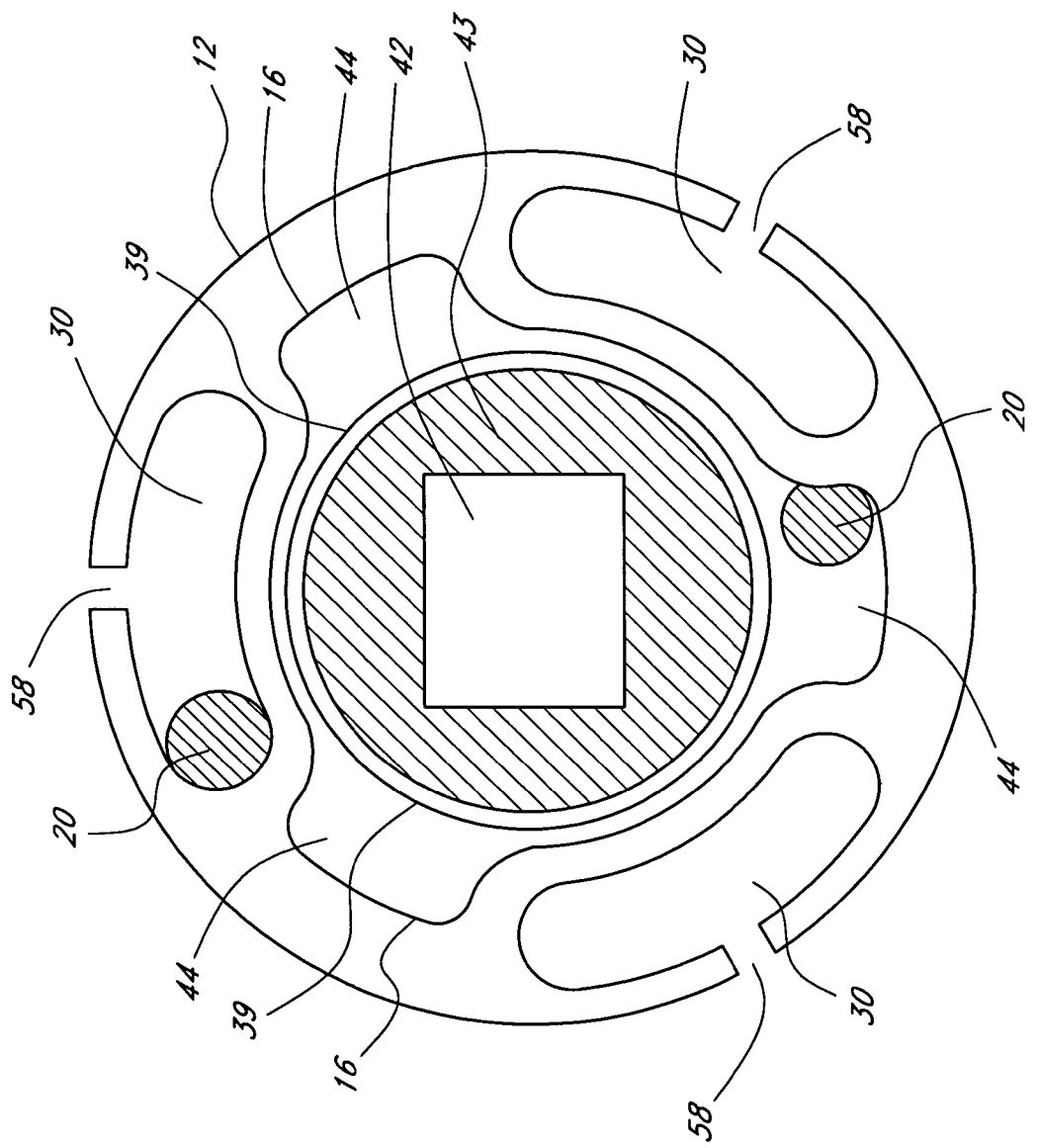
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery lumen 30 to the treatment site. For example, in one embodiment, fluid delivery ports 58 closer to the proximal region of the energy delivery section 18 have smaller diameters than fluid delivery ports 58 closer to the distal region of the energy delivery section 18, thereby allowing uniform delivery of fluid across the entire energy delivery section 18.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120° increments for a three-lumen configuration), thereby providing uniform cooling fluid flow over the inner core 34. Such a configuration is desired to remove unwanted thermal energy at the treatment site. As will be explained below, the flow rate of the cooling fluid and the power to the ultrasound assembly 42 can be adjusted to maintain the temperature of the inner core energy delivery section 41 within a desired range.

In an exemplary embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In an exemplary embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by configuring the inner core 34 to have a length that is less than the length of the tubular body 12. In other embodiments, a protrusion is formed on the inner surface 16 of the tubular body 12 in the distal region 15, thereby preventing the inner core 34 from passing through the distal exit port 29.

In still other embodiments, the catheter 10 further comprises an occlusion device (not shown) positioned at the distal exit port 29. The occlusion device preferably has a reduced inner diameter that can accommodate a guidewire, but that is less than the outer diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead wire (not shown) which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
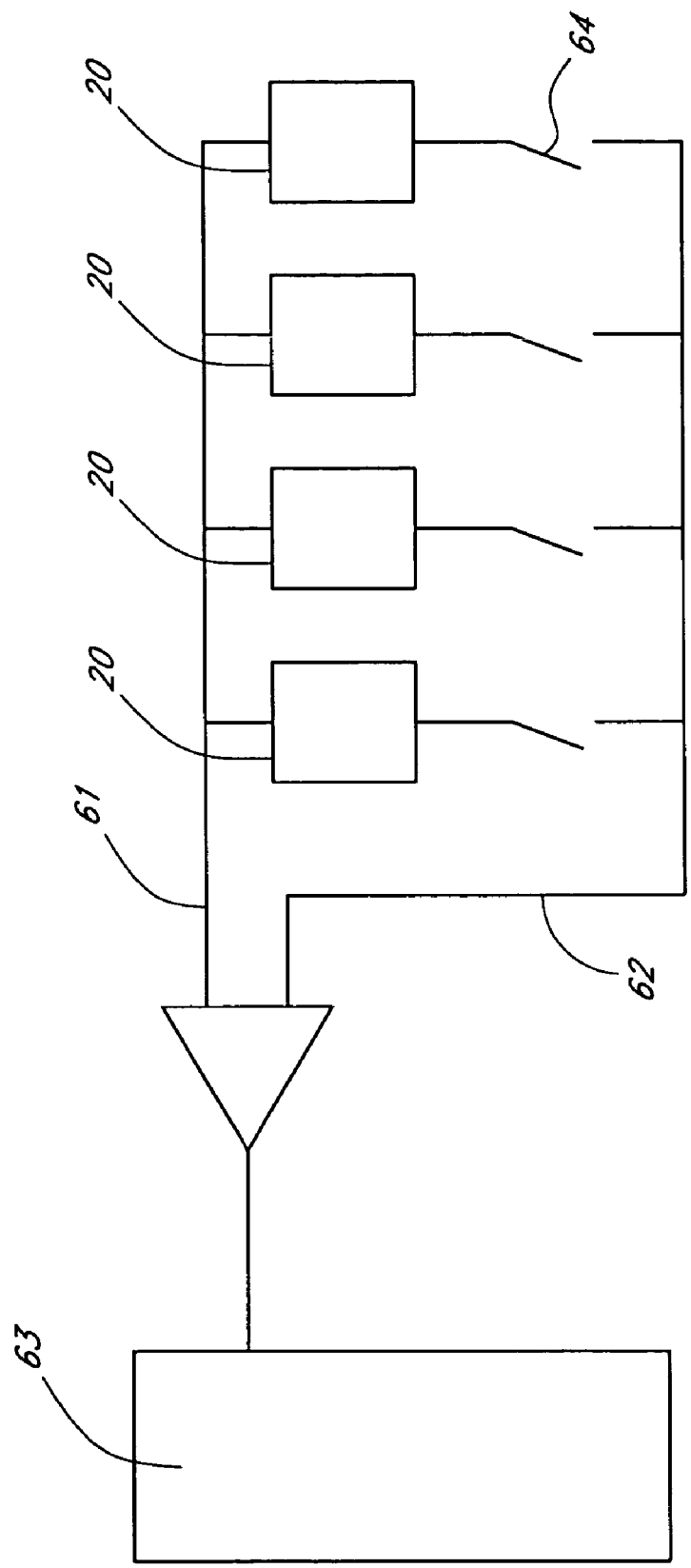
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires pass through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
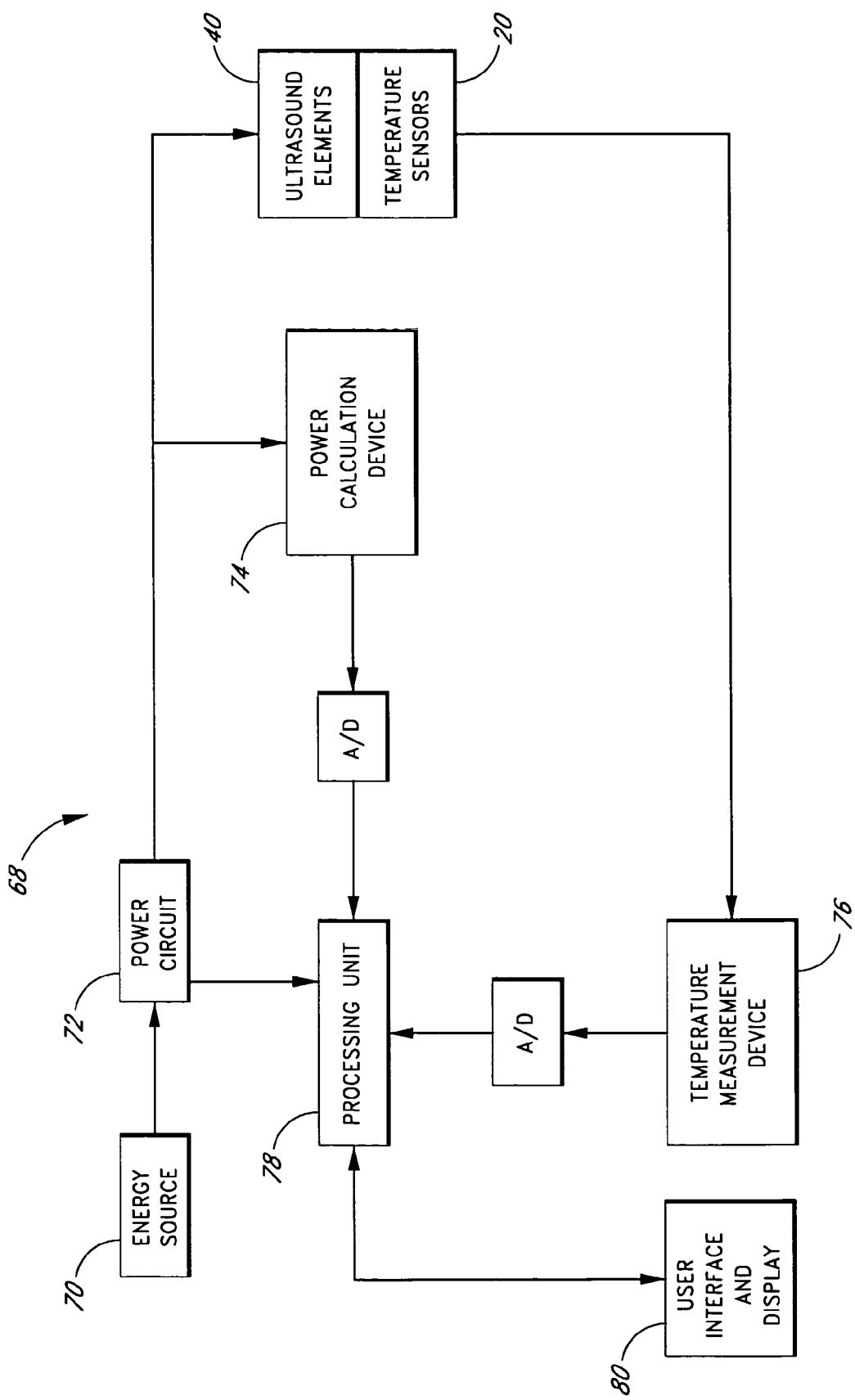
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members 40 can be operated in a pulsed mode. For example, in one embodiment, the time average power supplied to the ultrasound radiating members 40 is preferably between about 0.1 watts and 2 watts and more preferably between about 0.5 watts and 1.5 watts. In certain preferred embodiments, the time average power is approximately 0.6 watts or 1.2 watts. The duty cycle is preferably between about 1% and 50% and more preferably between about 5% and 25%. In certain preferred embodiments, the duty ratio is approximately 7.5% or 15%. The pulse averaged power is preferably between about 0.1 watts and 20 watts and more preferably between approximately 5 watts and 20 watts. In certain preferred embodiments, the pulse averaged power is approximately 8 watts and 16 watts. The amplitude during each pulse can be constant or varied.

In one embodiment, the pulse repetition rate is preferably between about 5 Hz and 150 Hz and more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

In one particular embodiment, the ultrasound radiating members 40 are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating members 40 used with the electrical parameters described herein preferably has an acoustic efficiency greater than 50% and more preferably greater than 75%. The ultrasound radiating members 40 can be formed a variety of shapes, such as, cylindrical (solid or hollow), flat, bar, triangular, and the like. The length of the ultrasound radiating members 40 is preferably between about 0.1 cm and about 0.5 cm. The thickness or diameter of the ultrasound radiating members 40 is preferably between about 0.02 cm and about 0.2 cm.

Figure 11A:
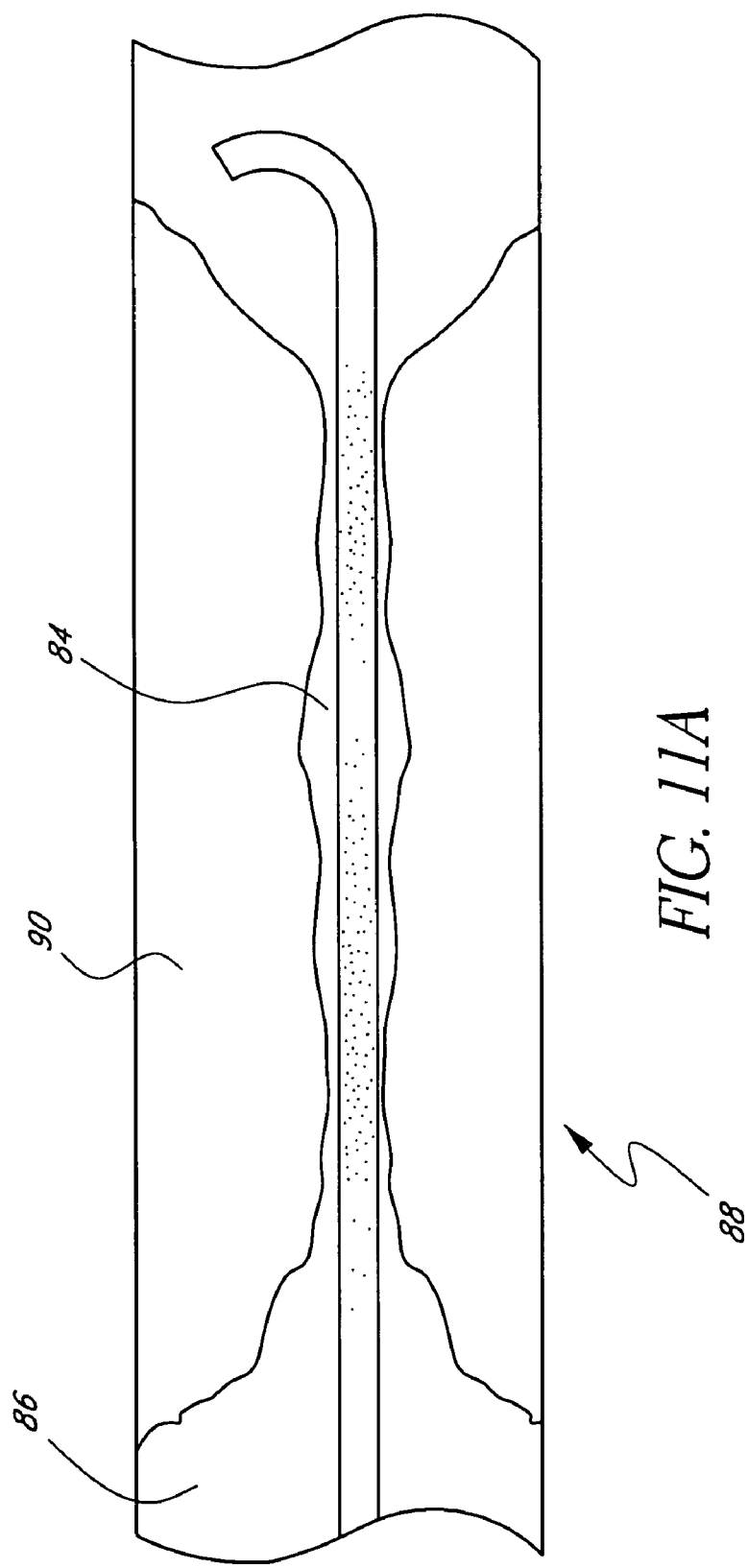
FIG. 11A is a side view of a treatment site.

FIGS. 11A through 11D illustrate an exemplary method for using the ultrasonic catheter 10. As illustrated in FIG. 11A, a guidewire 84 similar to a guidewire used in typical angioplasty procedures is directed through a patient's vessels 86 to a treatment site 88 which includes a clot 90. The guidewire 84 is directed through the clot 90. Suitable vessels 86 include, but are not limited to, the large periphery and the small cerebral blood vessels of the body. Additionally, as mentioned above, the ultrasonic catheter 10 also has utility in various imaging applications or in applications for treating and/or diagnosing other diseases in other body parts.

Figure 11B:
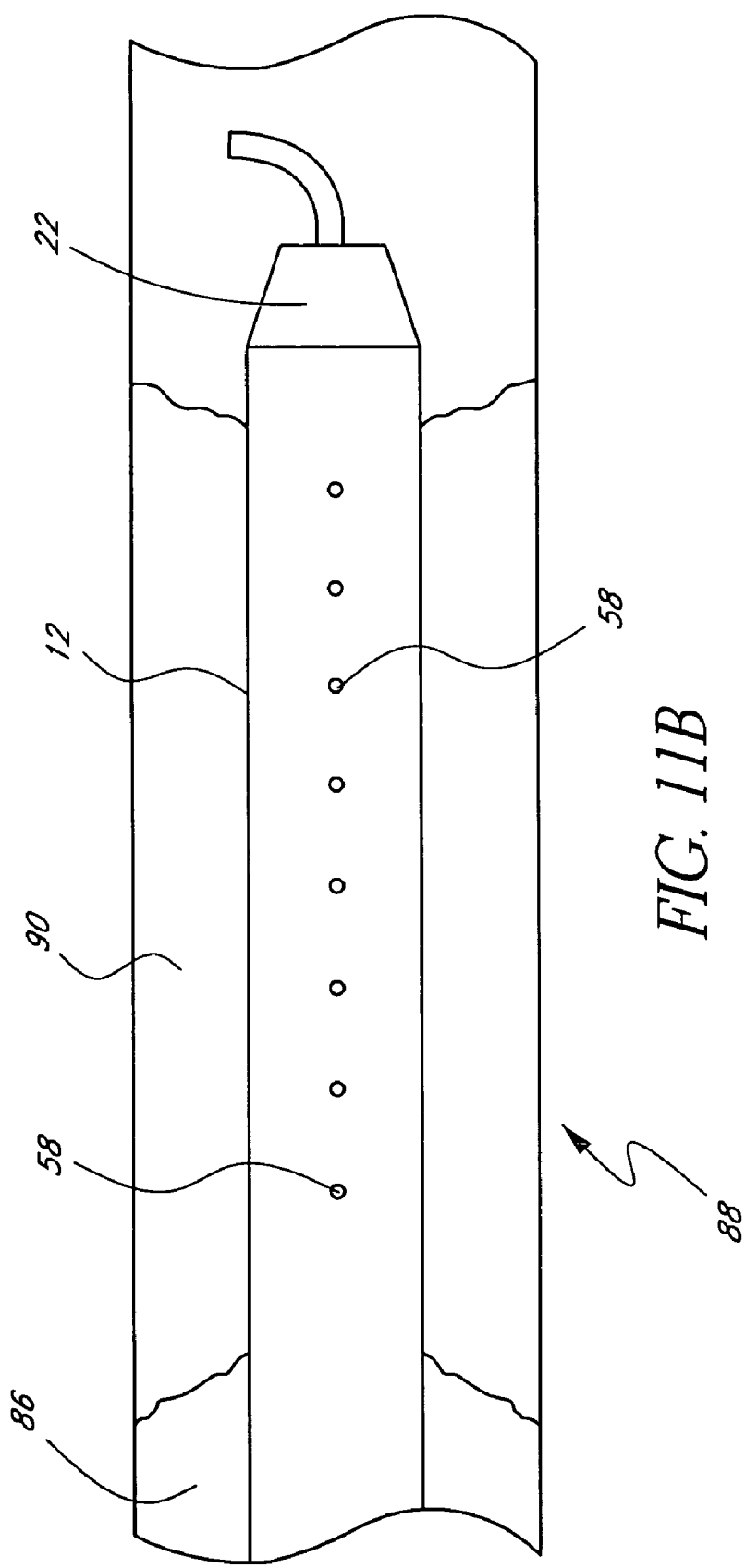
FIG. 11B is a side view of the distal end of an ultrasonic catheter positioned at the treatment site of FIG. 11A.

As illustrated in FIG. 11B, the tubular body 12 is slid over and is advanced along the guidewire 84 using conventional over-the-guidewire techniques. The tubular body 12 is advanced until the energy delivery section 18 of the tubular body 12 is positioned at the clot 90. In certain embodiments, radiopaque markers (not shown) are positioned along the energy delivery section 18 of the tubular body 12 to aid in the positioning of the tubular body 12 within the treatment site 88.

Figure 11C:
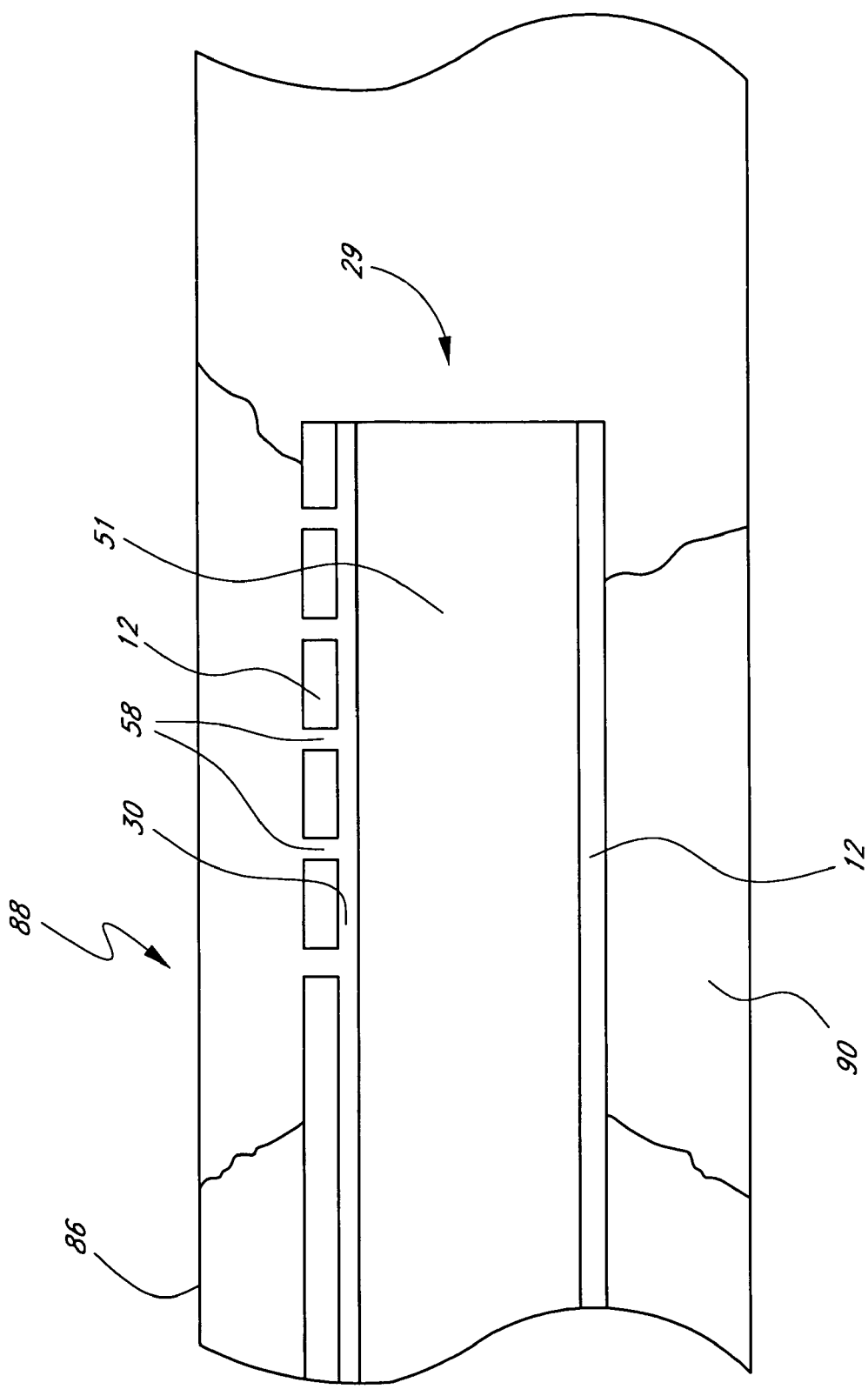
FIG. 11C is a cross-sectional view of the distal end of the ultrasonic catheter of FIG. 11B positioned at the treatment site before a treatment.

As illustrated in FIG. 11C, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

Figure 11D:
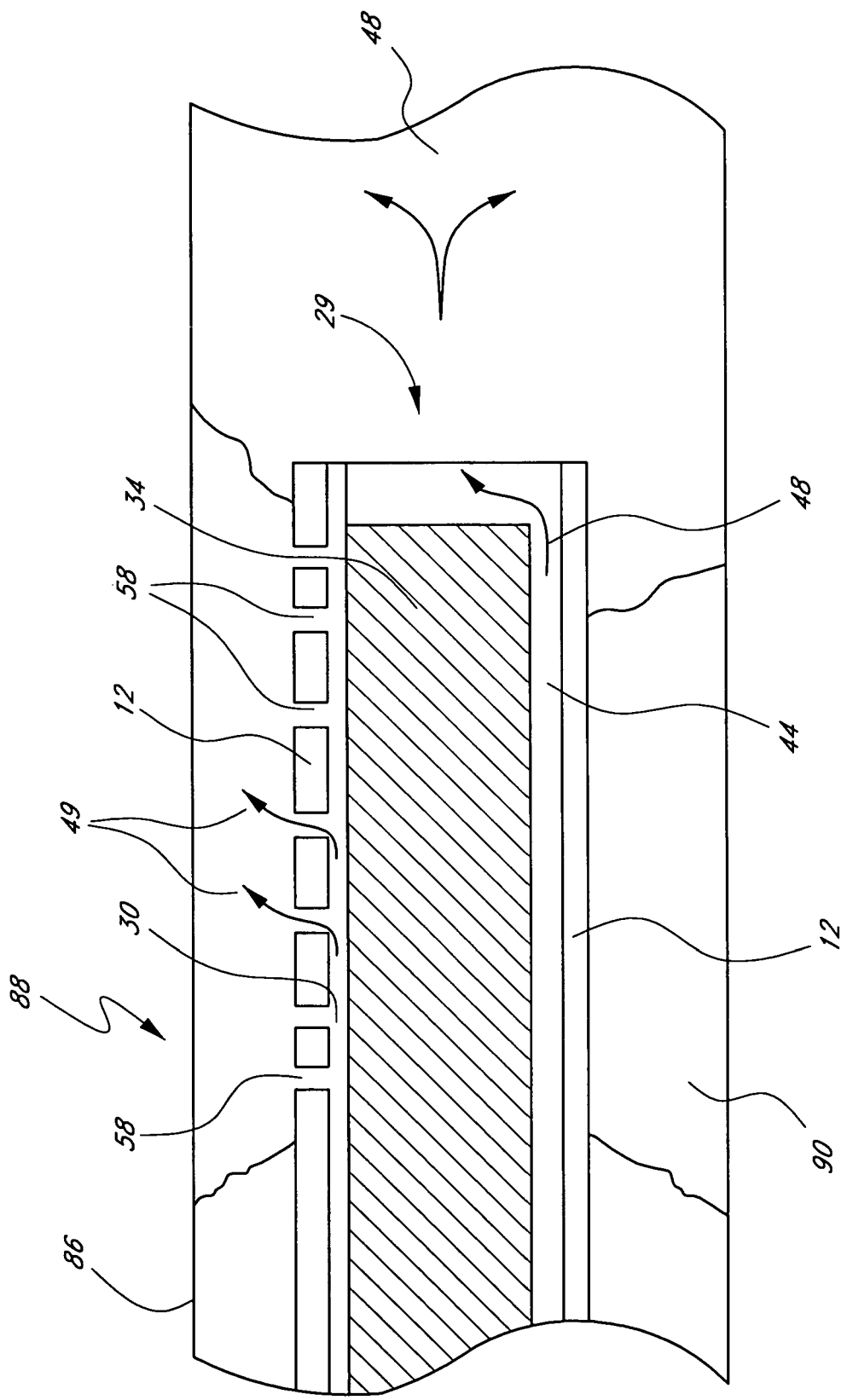
FIG. 11D is a cross-sectional view of the distal end of the ultrasonic catheter of FIG. 11C, wherein an inner core has been inserted into the tubular body to perform a treatment.

As illustrated in FIG. 11D, the inner core 34 is then inserted into the tubular body 12 until the ultrasound assembly is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, in one embodiment, suitable ultrasonic energy is delivered with a frequency between about 20 kHz and about 20 MHz.

In a certain embodiment, the ultrasound assembly 42 comprises sixty ultrasound radiating members 40 spaced over a length between approximately 30 cm and 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicate that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than as described above. In an exemplary embodiment, the therapeutic compound and ultrasonic energy are applied until the clot 90 is partially or entirely dissolved. Once the clot 90 has been dissolved to the desired degree, the tubular body 12 and the inner core 34 are withdrawn from the treatment site 88.

Overview of a Small Vessel Ultrasound Catheter.

Over the years, numerous types of ultrasound catheters have been proposed for various therapeutic purposes. However, none of the existing ultrasound catheters is well adapted for effective use within small blood vessels in the distal anatomy. For example, in one primary shortcoming, the region of the catheter on which the ultrasound assembly is located (typically along the distal end portion) is relatively rigid and therefore lacks the flexibility necessary for navigation through difficult regions of the distal anatomy. Furthermore, it has been found that it is very difficult to manufacture an ultrasound catheter having a sufficiently small diameter for use in small vessels while providing adequate pushability and torqueability. Still further, it has been found that the distal tip of an ultrasound catheter can easily damage the fragile vessels of the distal anatomy during advancement through the patient's vasculature.

Accordingly, an urgent need exists for an improved ultrasound catheter that is capable of safely and effectively navigating small blood vessels. It is also desirable that such a device be capable of delivering adequate ultrasound energy to achieve the desired therapeutic purpose. It is also desirable that such a device be capable of accessing a treatment site in fragile distal vessels in a manner that is safe for the patient and that is not unduly cumbersome. The present invention addresses these needs.

The advancement of an ultrasound catheter through a blood vessel to a treatment site can be difficult and dangerous, particularly when the treatment site is located within a small vessel in the distal region of a patient's vasculature. To reach the treatment site, it is often necessary to navigate a tortuous path around difficult bends and turns. During advancement through the vasculature, bending resistance along the distal end portion of the catheter can severely limit the ability of the catheter to make the necessary turns. Moreover, as the catheter is advanced, the distal tip of the catheter is often in contact with the inner wall of the blood vessel. The stiffness and rigidity of the distal tip of the catheter may lead to significant trauma or damage to the tissue along the inner wall of the blood vessel. As a result, advancement of an ultrasound catheter through small blood vessels can be extremely hazardous. Therefore, a need exists for an improved ultrasound catheter design that allows a physician to more easily navigate difficult turns in small blood vessels while minimizing trauma and/or damage along the inner walls of the blood vessels. To address this need, preferred embodiments of the present invention described herein provide an ultrasound catheter that is well suited for use in the treatment of small blood vessels or other body lumens having a small inner diameter.

As used herein, the term "ultrasound energy" is a broad term and is used in its ordinary sense and means, without limitation, mechanical energy transferred through pressure or compression waves with a frequency greater than about 20 kHz. In one embodiment, the waves of the ultrasound energy have a frequency between about 500 kHz and 20 MHz and in another embodiment between about 1 MHz and 3 MHz. In yet another embodiment, the waves of the ultrasound energy have a frequency of about 3 MHz.

As used herein, the term "catheter" is a broad term and is used in its ordinary sense and means, without limitation, an elongate flexible tube configured to be inserted into the body of a patient, such as, for example, a body cavity, duct or vessel.

Figure 12:
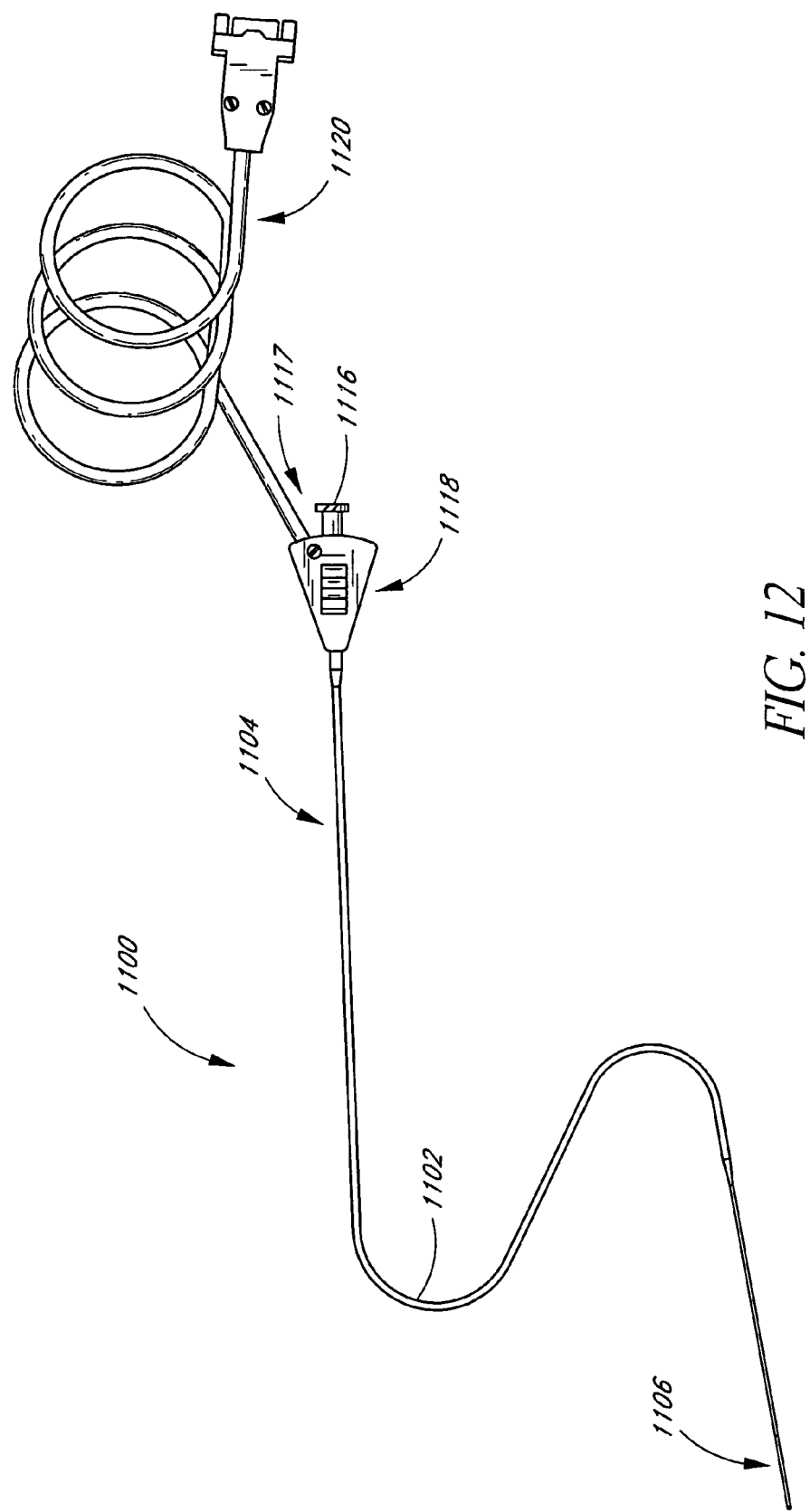
FIG. 12 is a side view of an ultrasound catheter that is particularly well suited for insertion into small blood vessels of the human body.

Referring now to FIGS. 12 through 13B, for purposes of illustration, preferred embodiments of the present invention provide an ultrasound catheter 1100 that is particularly well suited for use within small vessels of the distal anatomy, such as, for example, in the remote, small diameter, neurovasculature in the brain.

As shown in FIGS. 12 and 13A, the ultrasound catheter 1100 generally comprises a multi-component tubular body 1102 having a proximal end 1104 and a distal end 1106. The tubular body 1102 and other components of the catheter 1100 can be manufactured in accordance with any of a variety of techniques well know in the catheter manufacturing field. As discussed in more detail below, suitable material dimensions can be readily selected taking into account the natural and anatomical dimensions of the treatment site and of the desired percutaneous access site.

Preferably, the tubular body 1102 can be divided into at least three sections of varying stiffness. The first section, which preferably includes the proximal end 1104, is generally more stiff than a second section, which lies between the proximal end 1104 and the distal end 1106 of the catheter. This arrangement facilitates the movement and placement of the catheter 1102 within small vessels. The third section, which includes ultrasound radiating element 1124, is generally stiffer than the second section due to the presence of the ultrasound radiating element 1124.

In each of the embodiments described herein, the assembled ultrasound catheter preferably has sufficient structural integrity, or "pushability," to permit the catheter to be advanced through a patient's vasculature to a treatment site without buckling or kinking. In addition, the catheter has the ability to transmit torque, such that the distal portion can be rotated into a desired orientation after insertion into a patient by applying torque to the proximal end.

The elongate flexible tubular body 1102 comprises an outer sheath 1108 (see FIG. 13A) that is positioned upon an inner core 1110. In an embodiment particularly well suited for small vessels, the outer sheath 1108 comprises extruded PEBAX, PTFE, PEEK, PE, polyimides, braided polyimides and/or other similar materials. The distal end portion of the outer sheath 1108 is adapted for advancement through vessels having a very small diameter, such as those in the neurovasculature of the brain. Preferably, the distal end portion of the outer sheath 1108 has an outer diameter between about 2 and 5 French. More preferably, the distal end portion of the outer sheath 1108 has an outer diameter of about 2.8 French. In one preferred embodiment, the outer sheath 1108 has an axial length of approximately 150 centimeters.

In other embodiments, the outer sheath 1108 can be formed from a braided tubing formed of, by way of example, high or low density polyethylenes, urethanes, nylons, and the like. Such an embodiment enhances the flexibility of the tubular body 1102. For enhanced pushability and torqueability, the outer sheath 1108 may be formed with a variable stiffness from the proximal to the distal end. To achieve this, a stiffening member may be included along the proximal end of the tubular body 1102.

The inner core 1110 defines, at least in part, a delivery lumen 1112, which preferably extends longitudinally along the entire length of the catheter 1100. The delivery lumen 1112 has a distal exit port 1114 and a proximal access port 1116. Referring again to FIG. 12, the proximal access port 1116 is defined by drug inlet port 1117 of a back end hub 1118, which is attached to the proximal end 1104 of the other sheath 1108. The illustrated back end hub 1118 is preferably attached to a control box connector 1120, the utility of which will be described in more detail below.

The delivery lumen 1112 is preferably configured to receive a guide wire (not shown). Preferably, the guidewire has a diameter of approximately 0.008 to 0.012 inches. More preferably, the guidewire has a diameter of about 0.010 inches. The inner core 1110 is preferably formed from polymide or a similar material which, in some embodiments, can be braided to increase the flexibility of the tubular body 1102.

With particular reference to FIGS. 13A and 13B, the distal end 1106 of the catheter 1102 preferably includes the ultrasound radiating element 1124. In the illustrated embodiment, the ultrasound radiating element 1124 comprises an ultrasound transducer, which converts, for example, electrical energy into ultrasound energy. In a modified embodiment, the ultrasound energy can be generated by an ultrasound transducer that is remote from the ultrasound radiating element 1124 and the ultrasound energy can be transmitted via, for example, a wire to the ultrasound radiating element 1124.

In the embodiment illustrated in FIGS. 13A and 13B, the ultrasound radiating element 1124 is configured as a hollow cylinder. As such, the inner core 1110 can extend through the lumen of the ultrasound radiating element 1124. The ultrasound radiating element 1124 can be secured to the inner core 1110 in any suitable manner, such as with an adhesive. A potting material may also be used to further secure the mounting of the ultrasound radiating element along the central core.

In other embodiments, the ultrasound radiating element 1124 can be configured with a different shape. For example, the ultrasound radiating element may take the form of a solid rod, a disk, a solid rectangle or a thin block. Still further, the ultrasound radiating element 1124 may comprise a plurality of smaller ultrasound radiating elements. The illustrated arrangement is the generally preferred configuration because it provides for enhanced cooling of the ultrasound radiating element 1124. For example, in one preferred embodiment, a drug solution can be delivered through the delivery lumen 1112. As the drug solution passes through the lumen of the ultrasound radiating element, the drug solution may advantageously provide a heat sink for removing excess heat generated by the ultrasound radiating element 1124. In another embodiment, a return path can be formed in the space 1138 between the outer sheath and the inner core such that coolant from a coolant system can be directed through the space 1138.

The ultrasound radiating element 1124 is preferably selected to produce ultrasound energy in a frequency range that is well suited for the particular application. Suitable frequencies of ultrasound energy for the applications described herein include, but are not limited to, from about 20 kHz to about 20 MHz. In one embodiment, the frequency is between about 500 kHz and 20 MHz and in another embodiment from about 1 MHz and about 3 MHz. In yet another embodiment, the ultrasound energy has a frequency of about 3 MHz.

As mentioned above, in the illustrated embodiment, ultrasound energy is generated from electrical power supplied to the ultrasound radiating element 1124. The electrical power can be supplied through the controller box connector 1120, which is connected to a pair wires 1126, 1128 that extend through the catheter body 1102. The electrical wires 1126, 1128 can be secured to the inner core 1110, lay along the inner core 1110 and/or extend freely in the space between the inner core 1110 and the outer sheath 1108. In the illustrated arrangement, the first wire 1126 is connected to the hollow center of the ultrasound radiating element 1124 while the second wire 1128 is connected to the outer periphery of the ultrasound radiating element 1124. The ultrasound radiating element 1124 is preferably, but is not limited to, a transducer formed of a piezolectric ceramic oscillator or a similar material.

With continued reference to FIGS. 13A and 13B, the distal end 1104 of the catheter 1100 preferably includes a sleeve 1130, which is generally positioned about the ultrasound radiating element 1124. The sleeve 1130 is preferably constructed from a material that readily transmits ultrasound energy. Suitable materials for the sleeve 1130 include, but are not limited to, polyolefins, polyimides, polyester and other materials having a relatively low impedance to ultrasound energy. Low ultrasound impedance materials are materials that readily transmit ultrasound energy with minimal absorption of the ultrasound energy. The proximal end of the sleeve 1130 can be attached to the outer sheath 1108 with an adhesive 1132. To improve the bonding of the adhesive 1132 to the outer sheath 1108, a shoulder 1127 or notch may be formed in the outer sheath for attachment of the adhesive thereto. Preferably, the outer sheath 1108 and the sleeve 1130 have substantially the same outer diameter.

In a similar manner, the distal end of the sleeve 1130 can be attached to a tip 1134. In the illustrated arrangement, the tip 1134 is also attached to the distal end of the inner core 1110. Preferably, the tip is between about 0.5 and 4.0 millimeters in length. More preferably, the tip is about 2.0 millimeters in length. As illustrated, the tip is preferably rounded in shape to reduce trauma or damage to tissue along the inner wall of a blood vessel or other body structure during advancement toward a treatment site.

With continued reference to FIG. 13B, the catheter 1100 preferably includes at least one temperature sensor 1136 along the distal end 1106. The temperature sensor 1136 is preferably located on or near the ultrasound radiating element 1124. Suitable temperature sensors include but are not limited to, diodes, thermistors, thermocouples, resistance temperature detectors (RTDs), and fiber optic temperature sensors that used thermalchromic liquid crystals. The temperature sensor is preferably operatively connected to a control box (not shown) through a control wire, which extends through the catheter body 1102 and back end hub 1118 and is operatively connected to a control box through the control box connector 1120. The control box preferably includes a feedback control system having the ability to monitor and control the power, voltage, current and phase supplied to the ultrasound radiating element. In this manner, the temperature along the relevant region of the catheter can be monitored and controlled for optimal performance. Details of the control box can be found in Assignee's co-pending provisional application entitled CONTROL POD FOR ULTRASONIC CATHETER, Application Ser. No. 60/336,630, filed Dec. 3, 2001, which is incorporated by reference in its entirety.

In one exemplary application of the ultrasound catheter 1100 described above, the apparatus may be used to remove a thrombotic occlusion from a small blood vessel. In one preferred method of use, a free end of a guidewire is percutaneously inserted into the patient's vasculature at a suitable first puncture site. The guidewire is advanced through the vasculature toward a treatment site wherein the blood vessel is occluded by the thrombus. The guidewire wire is preferably then directed through the thrombus.

After advancing the guidewire to the treatment site, the catheter 1100 is thereafter percutaneously inserted into the vasculature through the first puncture site and is advanced along the guidewire towards the treatment site using traditional over-the-guidewire techniques. The catheter 1100 is advanced until the distal end 1106 of the catheter 1100 is positioned at or within the occlusion. The distal end 1106 of the catheter 1100 may include one or more radiopaque markers (not shown) to aid in positioning the distal end 1106 within the treatment site.

After placing the catheter, the guidewire can then be withdrawn from the delivery lumen 1112. A drug solution source (not shown), such as a syringe with a Luer fitting, is attached to the drug inlet port 1117 and the controller box connector 1120 is connected to the control box. As such, the drug solution can be delivered through the delivery lumen 1112 and out the distal access port 1114 to the thrombus. Suitable drug solutions for treating a thrombus include, but are not limited to, an aqueous solution containing heparin, urokinase, streptokinase, and/or tissue plasminogen activator (TPA).

The ultrasound radiating element 1124 is activated to emit ultrasound energy from the distal end 1106 of the catheter 1100. As mentioned above, suitable frequencies for the ultrasound radiating element 1124 include, but are not limited to, from about 20 kHz to about 20 MHz. In one embodiment, the frequency is between about 500 kHz and 20 MHz and in another embodiment between about 1 MHz and 3 MHz. In yet another embodiment, the ultrasound energy is emitted at a frequency of about 3 MHz. The drug solution and ultrasound energy are applied until the thrombus is partially or entirely dissolved. Once the thrombus has been dissolved to the desired degree, the catheter 1100 is withdrawn from the treatment site.

Overview of Ultrasonic Catheter with Axial Energy Field.

As described above, in certain applications, it is desirable to project an axial (or "forward-facing") ultrasonic energy field from the distal end of an ultrasonic catheter. For example, a high-power, forward-facing ultrasonic energy field is useful in the dissolution of aged blood clot located in the coronary vasculature.

Figure 14:
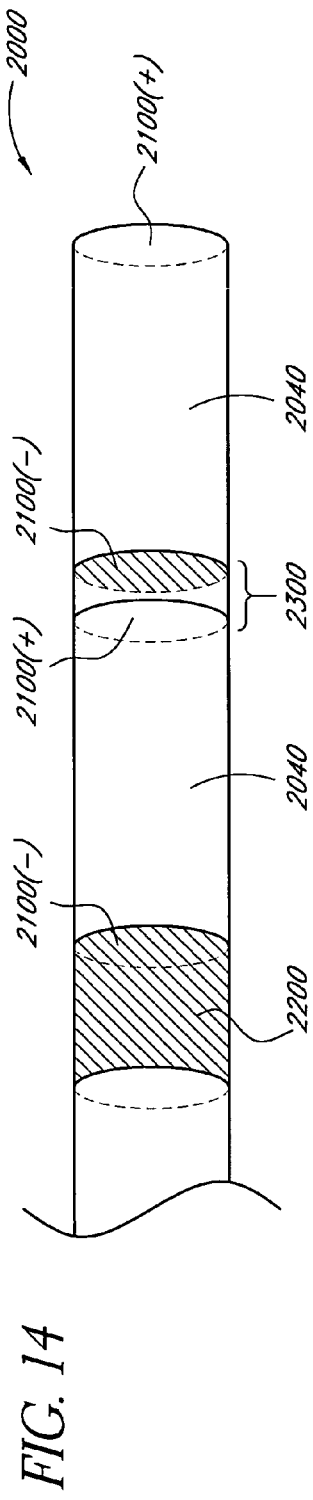
FIG. 14 is a side view of a distal end of an ultrasonic catheter configured to produce a forward-facing ultrasonic energy field and including solid cylindrical ultrasound radiating members.

FIG. 14 illustrates a distal end of an ultrasonic assembly 2000 configured to produce a forward-facing ultrasonic energy field. Such an ultrasonic assembly 2000 can be used, for example, with certain of the above-described catheters by passing the ultrasonic assembly 2000 through the catheter central lumen.

The ultrasonic assembly 2000 illustrated in FIG. 14 comprises a series of substantially cylindrical ultrasound radiating members 2040 with flat ends, wherein electrodes 2100 are mounted on each of the ultrasound radiating member flat ends. The ultrasound radiating members 2040 have a positive electrode 2100(+) and a negative electrode 2100(−). The ultrasonic assembly 2000 further comprises a proximal cap 2200 positioned adjacent the most proximal of the ultrasound radiating members 2040. Preferably, the proximal cap 2200 has a relatively high acoustic impedance compared to the other materials surrounding the ultrasound radiating members, such as the tubular body and the patient's vasculature. In one embodiment, the proximal cap may be made of such materials as copper, stainless steel, or plated copper or stainless steel. The cap 2200 preferably has an impedance in the range of about 35-110 MRayle and more preferably about 40-50 MRayl. This configuration causes the radiated ultrasonic energy field to be substantially forward-facing (that is, in the distal direction) along the axis of the ultrasonic assembly 2000.

In certain embodiments, as also illustrated in FIG. 14, the ultrasonic assembly further comprises one or more joints 2300 positioned between the individual ultrasound radiating members 2040. In this embodiment, the joints 2300 comprise an electrically insulating material to provide electrical insulation between successive ultrasound radiating members 2040. In an exemplary embodiment, the joints 2300 comprise a material having acoustic transmission properties (such as, for example, acoustic impedance and acoustic transmission velocity) that closely match the acoustic properties of the adjacent ultrasound radiating members 2040, while still providing additional flexibility to the ultrasonic assembly 2000. Non limiting examples of such materials are epotek 377 and hysol 2039/3561. Such materials preferably have an impedance in the range of about 1-30 MRayl and more preferably about 2-8 MRayl.

Figure 15:
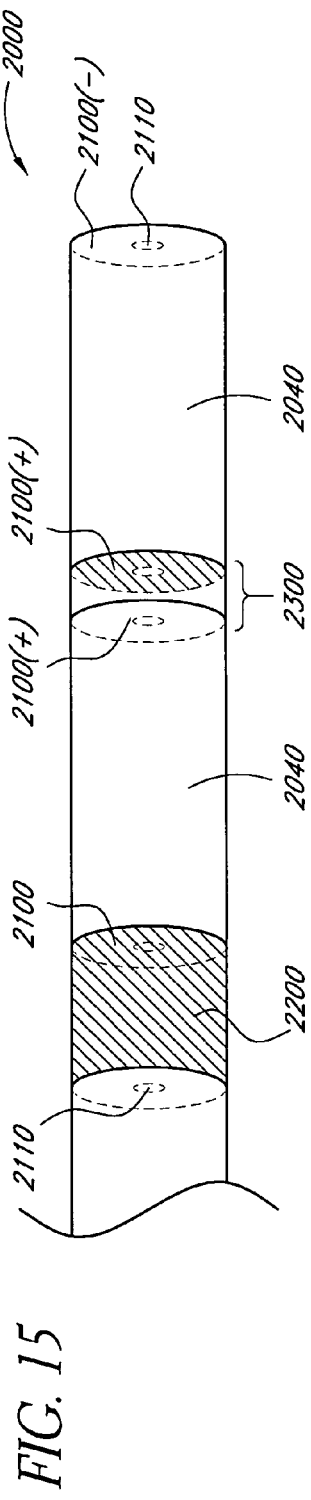
FIG. 15 is a side view of a distal end of an ultrasonic catheter configured to produce a forward-facing ultrasonic energy field including comprising hollow cylindrical ultrasound radiating members.

Although one orientation of electrode polarities is illustrated in FIG. 14, other electrode polarity orientations may be more appropriate in other embodiments. For example, a modified electrode polarity orientation is illustrated in FIG. 15. In this embodiment, the joints 2300 may be formed from an conductive material such that the two transducers 2040 form a "sandwich", "paired" design, sharing a common electrode as described above with reference to FIG. 7B.

FIG. 15 further illustrates that an ultrasonic assembly 2000 having a hollow core 2110 can be used in modified embodiments. Such embodiments are advantageous in applications where something is to be passed through the hollow core 2110 of the ultrasonic assembly 2000, such as for example, a guidewire, a cooling fluid or a therapeutic compound. The hollow core 2110 can be constructed in the ultrasound radiating members 2040, the electrodes 2100 and the joints 2300 using conventional techniques, such as for example, drilling or laser cutting. As mentioned above, in this embodiment, the joint 2300 may be made a conductive material. However, the hollow ultrasound radiating members illustrated in FIG. 15 can be used with the electrical configuration illustrated in FIG. 14. Additional information relating to ultrasound radiating members with hollow cores can be found in U.S. patent application Ser. No. 10/684,845, filed 14 Oct. 2003, the entire contents of which are hereby incorporated herein by reference.

Figure 16:
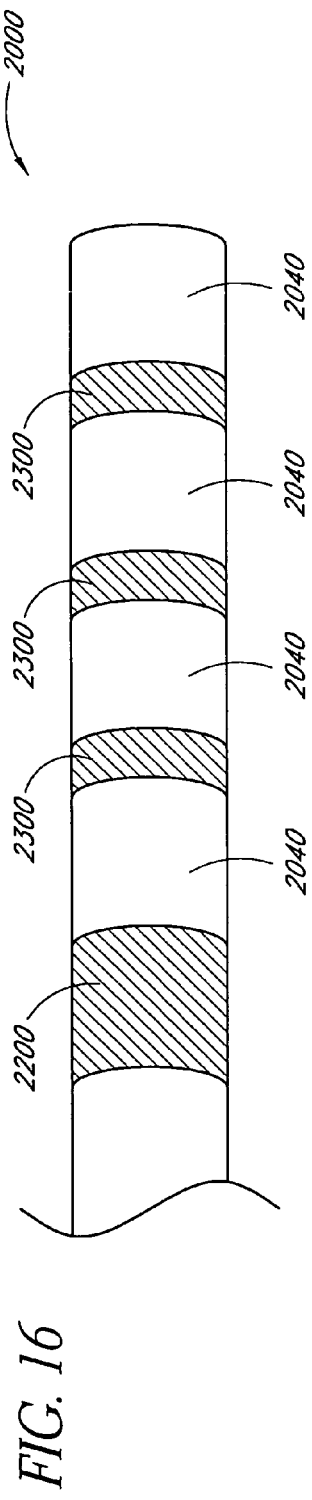
FIG. 16 is a side view of a distal end of an ultrasonic catheter configured to produce a forward-facing ultrasonic energy field and including a plurality of ultrasound radiating members.

FIG. 16 illustrates that the ultrasonic assembly 2000 illustrated in FIGS. 14 and 15 can be expanded to include more than two ultrasound radiating members 2040. This configuration facilitates formation of a forward-facing, or axial, energy field. In particular, ultrasonic energy generated by the ultrasound radiating members is focussed in the distal direction due to the presence of the high impedance cap 2200 at the proximal end of the ultrasound radiating members 2040. In such embodiments, the ultrasonic energy density in a region axially distal to the assembly 2000 is greater than the ultrasonic energy density in an annular region surrounding the assembly 2000.

Still referring to the exemplary embodiment illustrated in FIG. 16, joints 2300 are preferably positioned between each of the ultrasound radiating members 2040, thereby maintaining the overall flexibility of the ultrasonic assembly 2000. In addition, in an exemplary embodiment, electrodes (not shown for clarity) can be positioned on each flat end of each ultrasound radiating member, with adjacent electrodes separated by joints 2300. Thus, in certain embodiments, joints 2300 may comprise an electrically insulating material such as FIG. 14 or an electrically conducting material as in FIG. 15.

The ultrasonic assemblies described herein can be incorporated for use with both catheters and guidewires. For example, FIG. 17A illustrates a guidewire-mounted ultrasonic assembly configured to produce a forward-facing ultrasonic energy field. Specifically, a plurality of cylindrical ultrasound radiating members 2040 are mounted to the distal tip 2410 of a guidewire 2420. In an exemplary embodiment, the distal tip 2410 of the guidewire 2420 comprises a material with relatively high acoustic impedance (e.g., the high impedance materials described above), thus producing a substantially forward-facing ultrasonic energy field. Electrodes and joints (both not shown for clarity) can be positioned between the ultrasound radiating members 2040 as described above, and as required for particular applications. In such embodiments, the joints may be conductive or insulating depending on the desired electrical arrangement. In the embodiment illustrated in FIG. 17A, the ultrasound radiating members 2040 have substantially similar dimensions, as can be seen in the cross-sectional view of the end of the ultrasonic assembly shown in FIG. 17B.

FIG. 18A illustrates a modified embodiment of a guidewire-mounted ultrasonic assembly configured to produce a forward-facing ultrasonic energy field. In such embodiments, the ultrasound radiating members 2040 have decreasing dimensions toward the distal end of the assembly, thus providing a tapered tip. FIG. 18B is a cross-sectional view of the catheter guidewire of FIG. 18A taken along line 18B-18B. A tapered tip provides increased guidewire maneuverability, which is advantageous in certain applications. From this discussion, one of ordinary skill in the art will recognize that, in general, the guidewire 2420 need not have dimensions that match the dimensions of the ultrasound radiating members 2040. Again, as with the previous embodiments, the joints may be conductive or insulating.

FIG. 19A illustrates a modified embodiment of a guidewire-mounted ultrasonic assembly configured to produce a forward-facing ultrasonic energy field. In such embodiments, the ultrasound radiating members 2040 have rectangular dimensions, thus providing a square tip. In addition, FIG. 19A illustrates that, in such rectangular-dimensioned ultrasound assemblies, the electrodes 2100 can be positioned generally perpendicular to the joints 2030. FIG. 19B is a cross-sectional view of the catheter guidewire of FIG. 19A taken along line 19B-19B. In this configuration, a ultrasound radiating member group comprises two ultrasound radiating members separated by an electrode 2100. A plurality of ultrasound radiating member groups can be axially spaced along the guidewire 2420, with the groups being separated by the joints 2300.

Rectangular ultrasound radiating members can provide a reduced fabrication cost, which is advantageous in certain applications. In other embodiments, ultrasound radiating members having other cross-sectional shapes, such as other polygons or ovals, can be mounted to the distal tip 2410 of the guidewire 2420.

As described above, the various ultrasound assemblies illustrated in FIGS. 17A through 19B can be used with catheters as well as guidewires. Specifically, the ultrasound assemblies described above can be mounted directly on a catheter, or can be mounted on an inner core configured to be passed through a catheter central lumen. By positioning a high acoustic impedance material adjacent to the most proximal ultrasound radiating member, a substantially forward-facing ultrasonic energy field can be produced.

By manipulating the dimensions of the ultrasound radiating members comprising the ultrasonic assemblies described above, the resonant frequency of a particular ultrasonic assembly can be determined. Likewise, the resonant frequency of an ultrasonic assembly may be dependent on other factors, such as number of ultrasound radiating members. Thus, if a particular application requires a particular frequency of ultrasonic energy to be applied to the treatment site, the dimensions and number of ultrasound radiating members present within the ultrasonic assembly can be adjusted accordingly.

In certain embodiments, such as illustrated in FIG. 20, a joint 2300 is positioned between the most proximal ultrasound radiating member 2040 and the relatively high acoustic impedance material 2200. Such a configuration further increases flexibility, and therefore maneuverability, of the ultrasonic assembly. Again, the joints may be conductive or insulating depending upon the desired electrical configuration.

In modified embodiments, such as illustrated in FIG. 21, a horn 2250 comprising an acoustically matched material (e.g., a material having a similar acoustic property as the transducer) mounted to the distal tip of the catheter or guidewire. e.g., stainless steel and titanium Such a configuration would further enhance the production of a forward-facing ultrasonic energy field from the ultrasonic assembly. The characteristics of the ultrasonic energy field produced can be further manipulated by adjusting the dimensions and shape of the horn 2250. For example, appropriate shapes for horn 2250 include flat (illustrated in FIG. 21), blunt (illustrated in FIG. 22), short pointed (illustrated in FIG. 23) and long pointed (illustrated in FIG. 24). The addition of the horn 2250 is particularly advantageous with the sandwich type configurations described with reference, for example, to FIG. 15.

The various embodiments of the ultrasonic assemblies described herein offer several advantages. For example, the ultrasonic assemblies described herein can be operated at a reduced operational frequency as compared to conventional ultrasonic, assemblies having a comparable size. Lower operational frequencies advantageously increase the therapeutic effect of the ultrasonic energy. Additionally, the ultrasonic assemblies described herein can be operated with increased power output and widened forward dispersion as compared to conventional ultrasonic assemblies. Furthermore, the highly directional nature of the ultrasonic energy field produced by the ultrasonic assemblies described herein is advantageous in certain applications that require a targeted or focussed delivery of ultrasonic energy to the treatment site.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than treatment of vascular diseases.

I claim:

1. A catheter system for delivering ultrasonic energy to a treatment site within a body lumen, the catheter system comprising:
    a tubular body having a proximal end and a distal end; and
    an inner core configured for insertion into the tubular body, the inner core comprising:
        a first ultrasound radiating member axially separated from a separate and distinct second ultrasound radiating member by an intermediate flexible joint region, the first ultrasound radiating member positioned proximal to the second ultrasound radiating member, each ultrasound radiating member comprising a distal and proximal flat sides that extend generally perpendicular to a longitudinal axis of the tubular body and inner core, the distal and proximal flat sides of the ultrasound radiating member each including an electrode,
        an electrically conductive portion configured to allow a voltage difference to be applied to the electrodes of the first and second ultrasound radiating members, and
        a high acoustic impedance member, which is not one of the ultrasound radiating members, positioned proximal to the proximal flat side of the first ultrasound radiating member.

2. The catheter system of claim 1, wherein the high acoustic impedance member is positioned adjacent to one of the ultrasound radiating members.

3. The catheter system of claim 1, wherein an electrically insulating material is positioned in the intermediate flexible joint region.

4. The catheter system of claim 1, wherein the first ultrasound radiating member has a cross-sectional area that is greater than a cross-sectional area of the second ultrasound radiating member.

5. The catheter system of claim 1, wherein: the first ultrasound radiating member has a cross-sectional area that is greater than a cross-sectional area of the second ultrasound radiating member; and the first ultrasound radiating member is positioned proximal to the second ultrasound radiating member.

6. The catheter system of claim 1, wherein the high acoustic impedance member has an acoustic impedance that is greater than an acoustic impedance of the tubular body.

7. The catheter system of claim 1, wherein the inner core further comprises an elongate body configured to support the ultrasound radiating members.

8. The catheter system of claim 1, wherein the ultrasound radiating members have a cylindrical configuration.

9. The catheter system of claim 1, wherein the ultrasound radiating members have a rectangular configuration.

10. The catheter system of claim 1, wherein the inner core has a cross-sectional area that is greater than a cross-sectional area of the second ultrasound radiating member.

11. The catheter system of claim 1, wherein the inner core further comprises a hollow central lumen passing through the ultrasound radiating members.

12. The catheter system of claim 1, wherein the inner core further comprises a low impedance horn positioned distal to the ultrasound radiating members.

13. The catheter system of claim 1, wherein the inner core further comprises a low acoustic impedance horn positioned distal to the ultrasound radiating members, the low acoustic impedance horn having an acoustic impedance that is less than an acoustic impedance of the tubular body.

14. An ultrasound assembly comprising:
    an elongate member having a proximal region and a distal region opposite the proximal region;
    an ultrasound radiating member coupled to the distal region of the elongate member and having the same longitudinal axis as the distal region of the elongate member, the ultrasound radiating member configured to generate a distribution of ultrasonic energy that has a greater density in a region axially distal to the ultrasound radiating member than in an annular region surrounding the ultrasound radiating member, the ultrasound radiating member comprising a distal flat side and a proximal flat side that each extend generally perpendicular to a longitudinal axis of the elongate member, the distal and proximal flat sides of the ultrasound radiating member each including an electrode; and
    a high acoustic impedance member positioned adjacent the proximal flat side of the ultrasound radiating member.

15. The ultrasound assembly of claim 14, wherein the ultrasound assembly further comprises a flexible joint positioned between the ultrasound radiating member and the high acoustic impedance member.

16. The ultrasound assembly of claim 14, wherein the elongate member is a guidewire.

17. The ultrasound assembly of claim 14, wherein a plurality of ultrasound radiating members are positioned distal to the high acoustic impedance member.

18. The ultrasound assembly of claim 17, wherein at least two of the ultrasound radiating members are separated by an intermediate flexible joint region.

19. The ultrasound assembly of claim 18, wherein the intermediate flexible joint region is electrically insulating.

20. The ultrasound assembly of claim 14, further comprising a low acoustic impedance horn positioned distal to the ultrasound radiating member.

21. The ultrasound assembly of claim 14, further comprising a low acoustic impedance horn positioned distal to the ultrasound radiating member, the low acoustic impedance horn having a blunt-tip configuration.

22. The ultrasound assembly of claim 14, further comprising a low acoustic impedance horn positioned distal to the ultrasound radiating member, the low acoustic impedance horn having a pointed-tip configuration.

23. The ultrasound assembly of claim 14, wherein the ultrasound radiating member has a cylindrical cross-section with a cross-sectional area that is greater than cross-sectional area of the elongate member.

24. The ultrasound assembly of claim 14, wherein the ultrasound radiating member has a rectangular configuration.

25. The ultrasound assembly of claim 14, wherein the ultrasound radiating member and the elongate member have a continuous utility lumen passing therethrough.

26. The ultrasound assembly of claim 14, further comprising an electrically conductive portion configured to allow a voltage difference to be applied to the ultrasound radiating member.

* * * * *

UNITED STATES PATENT AND TRADEMARK OFFICE
CERTIFICATE OF CORRECTION

| | | |
|---|---|---|
| PATENT NO. | : 7,771,372 B2 | Page 1 of 1 |
| APPLICATION NO. | : 10/751843 | |
| DATED | : August 10, 2010 | |
| INVENTOR(S) | : Richard R. Wilson | |

It is certified that error appears in the above-identified patent and that said Letters Patent is hereby corrected as shown below:

Col. 24, Claim 23, line 2, after "than" insert --a--.

Signed and Sealed this
Twenty-eighth Day of June, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,771,372 B2 | Page 1 of 1 |
| APPLICATION NO. | : 10/751843 | |
| DATED | : August 10, 2010 | |
| INVENTOR(S) | : Richard R. Wilson | |

It is certified that error appears in the above-identified patent and that said Letters Patent is hereby corrected as shown below:

Col. 24, line 51 (Claim 23, line 2) after "than" insert --a--.

This certificate supersedes the Certificate of Correction issued June 28, 2011.

Signed and Sealed this
Twenty-sixth Day of July, 2011

David J. Kappos
*Director of the United States Patent and Trademark Office*